US006780996B2

(12) United States Patent
Boschelli et al.

(10) Patent No.: US 6,780,996 B2
(45) Date of Patent: Aug. 24, 2004

(54) PROCESS FOR THE PREPARATION OF 7-SUBSTITUTED-3 QUINOLINECARBONITRILES

(75) Inventors: Diane Harris Boschelli, New City, NY (US); Yanong Daniel Wang, Nanuet, NY (US); Steve Lawrence Johnson, Buffalo, NY (US); Dan Maarten Berger, New City, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 10/425,765

(22) Filed: Apr. 29, 2003

(65) Prior Publication Data

US 2003/0212276 A1 Nov. 13, 2003

Related U.S. Application Data

(60) Provisional application No. 60/376,456, filed on Apr. 30, 2002.

(51) Int. Cl.[7] .................... C07D 215/16; C07D 215/38; C07D 215/44
(52) U.S. Cl. .................. 546/153; 546/159; 546/160
(58) Field of Search ................... 546/153, 159, 546/160

(56) References Cited

U.S. PATENT DOCUMENTS

| 6,002,008 | A | 12/1999 | Wissner et al. | |
|---|---|---|---|---|
| 6,313,292 | B1 | 11/2001 | Showalter et al. | |
| 6,638,929 | B2 * | 10/2003 | DeMorin et al. | ........ 514/232.8 |

FOREIGN PATENT DOCUMENTS

| DE | 10017539 A1 | 11/2001 |
|---|---|---|
| WO | 97/26259 * | 7/1997 |
| WO | WO 00/18740 | 4/2000 |
| WO | WO 01/72711 A1 | 10/2001 |
| WO | WO 03/008409 | 1/2003 |
| WO | WO 98/43960 | 10/2003 |

OTHER PUBLICATIONS

Katritzky, A.R. "Comprehensive Heterocyclic Chemistry", vol. 2, pp. 59 and 359—362, 1984.*

Wissner, Allan et al.; J. of Med. Chem. (2000) 43(17), 3244–3256.

Zhang, Nan et al.; Bioorg. & Med. Chem. Lett., vol. 10 (2000), 2825–2828.

Boschelli, Diane H. et al.; J. Med. Chem. 2001, 44, 3965–3977.

* cited by examiner

*Primary Examiner*—D. Margaret Seaman
(74) *Attorney, Agent, or Firm*—Joy S. Goudie

(57) ABSTRACT

There is provided a process for the preparation of 7-substituted-3-quinolinecarbonitriles and intermediates useful in a process to prepare 7-substituted-3-quinolinecarbonitriles and pharmaceutically acceptable salts is described. Where 7-fluoro-4-oxo-1,4-dihydro-3-quinolinecarbonitrile is converted in three steps to 7-substituted-3-quinolinecarbonitriles which inhibit the action of certain protein kinases and are useful in the treatment of cancer.

14 Claims, No Drawings

PROCESS FOR THE PREPARATION OF 7-SUBSTITUTED-3 QUINOLINECARBONITRILES

This application claims priority from provisional application(s) serial No. 60/376456 filed on Apr. 30, 2002.

BACKGROUND OF THE INVENTION

This invention relates to a process for the preparation of 7-substituted-3-quinolinecarbonitriles and intermediates useful in a process to prepare 7-substituted-3-quinolinecarbonitriles and pharmaceutically acceptable salts thereof.

Protein kinases are enzymes that catalyze the transfer of a phosphate group from ATP to an amino acid residue, such as tyrosine, serine, threonine, or histidine on a protein. Regulation of these protein kinases is essential for the control of a wide variety of cellular events including proliferation and migration. Specific protein kinases have been implicated in diverse conditions including cancer [Traxler, P. M., Exp. Opin. Ther. Patents, 8, 1599 (1998); Bridges, A. J., Emerging Drugs, 3, 279 (1998)], restenosis [Mattsson, E., Trends Cardiovas. Med. 5, 200 (1995); Shaw, Trends Pharmacol. Sci. 16, 401 (1995)], atherosclerosis [Raines, E. W., Bioessays, 18, 271 (1996)], angiogenesis [Shawver, L. K., Drug Discovery Today, 2, 50 (1997); Folkman, J., Nature Medicine, 1, 27 (1995)] and osteoporosis [Boyce, J. Clin. Invest., 90, 1622 (1992)] and stroke (Paul, R. et al, Nature Medicine, 7(2), 222(2001). An effective preparation of compounds which are inhibitors of protein tyrosine kinases and are useful in the treatment of cancer is important.

The compounds disclosed in WO9843960 (U.S. Pat. No. 6,002,008) are 3-quinolinecarbonitrile derivatives which are inhibitors of protein tyrosine kinases and useful in the treatment of cancer. The aforementioned compounds have been prepared by processes which are effective for the initial preparation of targeted compounds. However, a new and effective alternate source of important intermediates useful in the preparation of 3-quinolinecarbontrile derivatives is desired. Additionally desired is an alternate process to prepare 7-substituted-3-quinolinecarbonitriles.

A further series of new 3-quinolinecarbonitriles which are also highly effective inhibitors of protein tyrosine kinases and useful in the treatment of cancer are disclosed in published application WO 00/18740. Suitable processes for the preparation of 3-quinolinecarbonitriles are described therein, however, there is still a need in the art for yet more suitable methods for the preparation of important intermediates and final products useful in the preparation of 3-quinolinecarbonitriles useful in the treatment of cancer.

Therefore, methods to prepare 7-substituted-3-quinolinecarbonitriles and intermediates to facilitate their preparation are of great value.

It is an object of this invention to provide an alternate process to prepare 7-substituted-3-quinolinecarbonitriles and intermediates useful in a process to prepare 7-substituted-3-quinolinecarbonitriles which are highly effective as inhibitors of protein kinases useful in the treatment of cancer.

It is an object of this invention to provide a novel process for the preparation of 7-substituted-3-quinolinecarbonitriles by displacement of the 7-fluoro group of 7-fluoro-4-(substituted amino)quinolinecarbonitriles.

It is a further object of this invention to provide a novel process for the preparation of 7-substituted-4-oxo-1,4-dihydro-3-quinolinecarbonitriles by displacement of the 7-fluoro group of 7-fluoro-4-oxo-1,4-dihydro-3-quinolinecarbonitriles.

BRIEF SUMMARY OF THE INVENTION

The present invention provides a process for the preparation of 7-substituted-3-quinolinecarbonitriles of Formula (I)

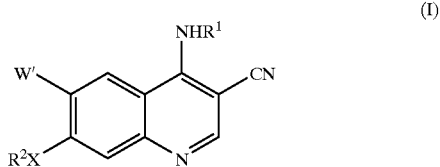

wherein:
X is selected from —O—, —S—, —NH—, and —NR$^{2'}$—;
W' is H or —OR$^3$;
q is an integer of 0–5;
m is an integer of 0–2;
n is an integer of 2–5;
R$^1$ is an alkyl group of 1 to 6 carbon atoms, a cycloalkyl group of 3 to 10 carbon atoms, or an aryl of 6 to 12 carbon atoms, or heteroaryl ring, said aryl or heteroaryl ring is optionally fused to an additional aryl or heteroaryl ring, wherein heteroaryl is defined as a 5 or 6 membered aromatic ring moiety containing at least one and up to 4 heteroatoms selected from O, S, and N; said aryl or heteroaryl rings optionally fused may optionally be substituted with 1 to 4 substituents independently selected from the group consisting of —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^4$, —OR$^4$, —NHR$^4$, —NR$^4$R$^4$, —S(O)$_m$R$^4$, —NHSO$_2$R$^4$, —R$^5$OH, —R$^5$OR$^4$, —R$^5$NH$_2$, —R$^5$NHR$^4$, —R$^5$NR$^4$R$^4$, —R$^5$SH, —R$^5$S(O)$_m$R$^4$, —NHR$^6$OH, —N(R$^4$)R$^6$OH, —N(R$^4$)R$^6$OR$^4$, —NHR$^6$NH$_2$, —NHR$^6$NHR$^4$, —NHR$^6$NR$^4$R$^4$, —N(R$^4$)R$^6$NH$_2$, —N(R$^4$)R$^6$NHR$^4$, —N(R$^4$)R$^6$NHR$^4$R$^4$, —OR$^6$OH, —OR$^6$OR$^4$, —OR$^6$NH$_2$, —OR$^6$NHR$^4$, —OR$^6$NR$^4$R$^4$, —OC(O)R$^4$, —NHC(O)R$^4$, —NHC(O)NHR$^4$, —OR$^5$C(O)R$^4$, —NHR$^5$C(O)R$^4$, —C(O)R$^4$, —C(O)OR$^4$, —C(O)NHR$^4$, —C(O)NR$^4$R$^4$, —R$^5$C(O)H, —R$^5$C(O)R$^4$, —R$^5$C(O)OH, —R$^5$C(O)OR$^4$, —R$^5$C(O)NH$_2$, —R$^5$C(O)NHR$^4$, —R$^5$C(O)NR$^4$R$^4$, —R$^5$OC(O)R$^4$, —R$^5$OC(O)NH$_2$, —R$^5$OC(O)NHR$^4$ and —R$^5$OC(O)NR$^4$R$^4$, and —YR$^7$ groups wherein Y is independently selected from —C(O)—, —C(O)O—, —OC(O)—, —C(O)NH—, —NHC(O)—, —NHSO$_2$—, —SO$_2$NH—, —C(OH)H—, —Q(C(R$^8$)$_2$)$_q$-, —(C(R$^8$)$_2$)$_q$-, —(C(R$^8$)$_2$)$_q$Q—, —C≡C—, cis- and trans —CH═CH— and cycloalkyl of 3–10 carbon atoms;
Q is —O—, —S(O)$_m$—, —NH—, or —NR$^9$—;
J is halogen selected from fluoro, chloro, bromo and iodo;
R$^2$, R$^{2'}$ and R$^3$ are each independently selected from an alkyl group of 1 to 6 carbon atoms, an alkenyl group of 2 to 6 carbon atoms or an alkynyl group of 2 to 6 carbon atoms, wherein each independent alkyl, alkenyl or alkynyl group is optionally substituted with —NO$_2$, cyano, or —QR$^4$, or R$^2$, R$^{2'}$ and R$^3$ are each independently selected from —(C(R$^8$)$_2$)$_q$-aryl, —(C(R$^8$)$_2$)$_q$-heteroaryl, —(C(R$^8$)$_2$)$_q$-heterocyclyl, —(C(R$^8$)$_2$)$_n$—Q—(C(R$^8$)$_2$)$_q$-aryl, —(C(R$^8$)$_2$)$_n$—Q—(C(R$^8$)$_2$)$_q$-heteroaryl, —(C(R$^8$)$_2$)$_n$—Q—(C(R$^8$)$_2$)$_q$-heterocyclyl, —(C(R$^8$)$_2$)$_n$—Q—(C(R$^8$)$_2$)$_n$—Q-aryl, —(C(R$^8$)$_2$)$_n$—Q—(C(R$^8$)$_2$)$_n$—Q-heteroaryl, and —(C(R$^8$)$_2$)$_n$—Q—(C(R$^8$)$_2$)$_n$—Q-heterocyclyl, wherein the heterocyclyl group may optionally be substituted on carbon or nitrogen with a group selected from —R$^4$, —(C(R$^8$)$_2$)$_q$-aryl, —(C(R$^8$)$_2$)$_q$-heteroaryl, —(C(R$^8$)$_2$)$_q$-heterocyclyl, —(C(R$^8$)$_2$)$_q$—SO$_2$R$^4$, or the heterocyclyl group may optionally be substituted on carbon by —(C(R$^8$)$_2$)$_q$—QR$^4$, or the heterocyclyl group may optionally be substituted on nitrogen by —(C(R$^8$)$_2$)$_n$—QR$^4$, and also wherein the aryl or heteroaryl group may optionally be substituted with a group selected from —NO$_2$, cyano, —R$^4$, —(C(R$^8$)2)$_q$-aryl, —(C(R$^8$)$_2$)$_q$-heteroaryl, —(C(R$^8$)$_2$)$_q$-heterocyclyl, —(C(R$^8$)$_2$)$_q$—SO$_2$R$^4$, and —(C(R$^8$)$_2$)$_q$—QR$^4$ and further provided that R$^2$ and R$^{2'}$ may optionally be taken together with the nitrogen to which they are attached, forming a heterocyclic ring, that optionally contains an additional heteroatom, selected from nitrogen, oxygen and sulfur, wherein said formed heterocyclic ring may optionally be substituted on carbon or nitrogen with a group —R$^4$, or said heterocyclic ring may optionally be substituted on carbon by —(C(R$^8$)$_2$)$_q$—QR$^4$, or said heterocyclic ring may optionally be substituted on nitrogen by —(C(R$^8$)$_2$)$_n$—QR$^4$;

R$^4$ is a monovalent group independently selected from alkyl of 1 to 6 carbon atoms, alkenyl of 2 to 6 carbon atoms, and alkynyl of 2 to 6 carbon atoms;

R$^5$ is a divalent group independently selected from alkyl of 1 to 6 carbon atoms, alkenyl of 2 to 6 carbon atoms, and alkynyl of 2 to 6 carbon atoms;

R$^6$ is a divalent alkyl group of 2 to 6 carbon atoms;

R$^7$ is a cycloalkyl ring of 3 to 10 carbon atoms optionally substituted with one or more alkyl groups of 1 to 6 carbon atoms or an aryl or heteroaryl ring, optionally fused to an additional aryl or heteroaryl ring, wherein said aryl or heteroaryl ring optionally fused, may optionally be substituted with 1 to 4 substituents selected from the group consisting of aryl, —CH$_2$-aryl, —NH-aryl, —O-aryl, —S(O)$_m$-aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^4$, —OR$^4$, —NHR$^4$, —NR$^4$R$^4$, —S(O)$_m$R$^4$, —NHSO$_2$R$^4$, —R$^5$OH, —R$^5$OR$^4$, —R$^5$NHR$_2$, —R$^5$NHR$^4$, —R$^5$NR$^4$R$^4$, —R$^5$SH, —R$^5$S(O)$_m$R$^4$, —NHR$^6$OH, —NHR$^6$OR$^4$, —N(R$^4$)R$^6$OH, —N(R$^4$)R$^6$OR$^4$, —NHR$^6$NH$_2$, —NHR$^6$NHR$^4$, —NHR$^6$NR$^4$R$^4$, —N(R$^4$)R$^6$NH$_2$, —N(R$^4$)R$^6$NHR$^4$, —N(R$^4$)R$^6$NHR$^4$R$^4$, —OR$^6$OH, —OR$^6$OR$^4$, —OR$^6$NH$_2$, —OR$^6$NHR$^4$, —OR$^6$NR$^4$R$^4$, —OC(O)R$^4$, —NHC(O)R$^4$, —NHC(O)NHR$^4$, —OR$^5$C(O)R$^4$, —NHR$^5$C(O)R$^4$, C(O)R$^4$, —C(O)OR$^4$, —C(O)NHR$^4$, —C(O)NR$^4$R$^4$, —R$^5$C(O)H, —R$^5$C(O)R$^4$, —R$^5$C(O)OH, —R$^5$C(O)OR$^4$, —R$^5$C(O)NH$_2$, —R$^5$C(O)NHR$^4$, —R$^5$C(O)NR$^4$R$^4$, —R$^5$OC(O)R$^4$, —R$^5$OC(O)NH$_2$, —R$^5$OC(O)NHR$^4$ and —R$^5$OC(O)NR$^4$R$^4$;

R$^8$ is independently —H or —R$^4$;

R$^9$ is a monovalent alkyl group of 1 to 6 carbon atoms; and pharmaceutically acceptable salts thereof;

which comprises the steps of:

a) reacting a 7-fluoro-4-oxo-1,4-dihydro-3-quinolinecarbonitrile of Formula (II)

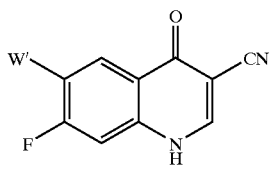

with a halogenating reagent of the formula PO(Z)$_3$ to provide a 7-fluoro-3-quinolinecarbonitrile 1 where Z is Cl or Br

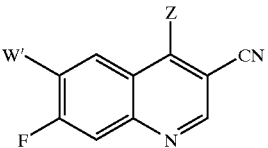

b) reacting a 7-fluoro-3-quinolinecarbonitrile of formula 1 of step a) with an amine of the formula R$^1$NH$_2$, e.g. in the presence of pyridine hydrochloride, to provide a 7-fluoro-4-(substituted amino)-3-quinolinecarbonitrile of formula 2

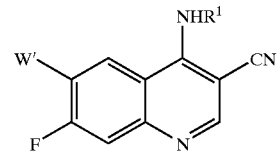

c) reacting a 7-fluoro-4-(substituted amino)-3-quinolinecarbonitrile of formula 2 of step b) with a compound of the formula R$^2$XH, where X is selected from —S—, —O—, —NH—, and —NR$^{2'}$— and where R$^{2'}$ and R$^2$ are as defined above or R$^2$ and R$^{2'}$ may optionally be taken together with the nitrogen to which each is attached to form a heterocyclic ring, and in the presence of a base, when X is —O— or —S—, to provide a 7-substituted-3-quinolinecarbonitrile of Formula (I)

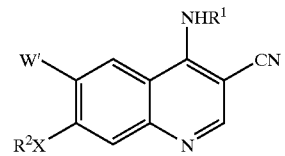

and if so desired converting a compound of Formula (I) to a corresponding pharmaceutically acceptable salt by conventional means, and if so desired, converting the corresponding pharmaceutically acceptable salt to a compound of Formula (I) by conventional means.

This invention also relates to a process for the preparation of 7-substituted-3-quinolinecarbonitriles of Formula (I)

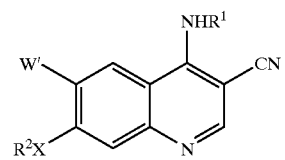

wherein the variables are as defined above, which comprises the step of: reacting a 7-fluoro-4-(substituted amino)-3-quinolinecarbonitrile of formula 2

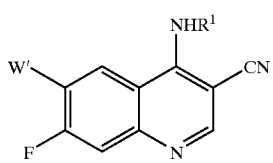

with a compound of the formula R²XH, where X is selected from —S—, —O—, —NH—, and —NR²'— and where R²' and R² are as defined above or R² and R²' may optionally be taken together with the nitrogen to which each is attached, to form a heterocyclic ring, and in the presence of a base, when X is —O— or —S—, to provide a 7-substituted-3-quinolinecarbonitrile of Formula (I),

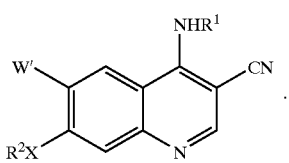

and if so desired converting a compound of Formula (I) to a corresponding pharmaceutically acceptable salt by conventional means, and if so desired, converting the corresponding pharmaceutically acceptable salt to a compound of Formula (I) by conventional means.

This invention further relates to a process for the preparation of 7-substituted-3-quinolinecarbonitriles of Formula (I)

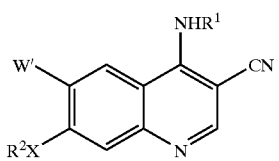

wherein the variables are as defined above, which comprises the steps of:

a) reacting a 7-fluoro-4-oxo-1,4-dihydro-3-quinolinecarbonitrile of Formula (II)

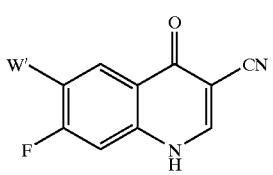

with a compound of the formula R²XH, where X is selected from —S—, —O—, —NH—, and —NR²'— and where R²' and R² are as defined above or R² and R²' may optionally be taken together with the nitrogen to which each is attached to form a heterocyclic ring, and in the presence of a base, when X is —O— or —S—, to provide a 7-substituted-4-oxo-1,4-dihydro-3-quinolinecarbonitrile of Formula 3

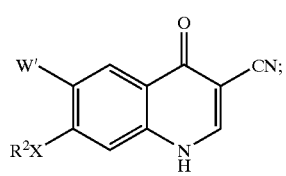

b) reacting a 7-substituted-4-oxo-1,4-dihydro-3-quinolinecarbonitrile of step a) with a halogenating reagent, e.g. of the formula PO(Z)₃, to provide a 7-substituted-4-halo-3-quinolinecarbonitrile 4 where Z is Cl or Br

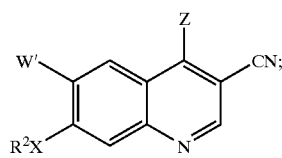

c) reacting a 7-substituted-4-halo-3-quinolinecarbonitrile of step b) with an amine R¹NH₂, e.g., in the presence of pyridine hydrochloride, to afford a 7-substituted-3-quinolinecarbonitrile of Formula (I)

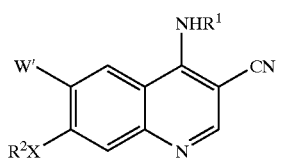

and if so desired converting a compound of Formula (I) to a corresponding pharmaceutically acceptable salt by conventional means, and if so desired, converting the corresponding pharmaceutically acceptable salt to a compound of Formula (I) by conventional means.

The invention further relates to a process for the preparation of 7-substituted-4-oxo-1,4-dihydro-3-quinolinecarbonitrile of Formula 3

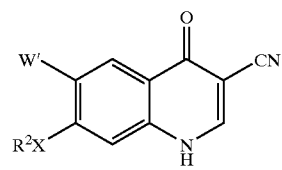

wherein the variables are as defined above,:

which comprises the step of:

reacting a 7-fluoro-4-oxo-1,4-dihydro-3-quinolinecarbonitrile of Formula (II)

II

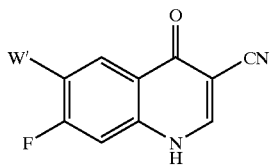

with a compound of the formula $R^2XH$, where X is selected from —S—, —O—, —NH—, and —$NR^{2'}$— and where $R^{2'}$ and $R^2$ may optionally be taken together with the nitrogen to which each is attached, to form a heterocyclic ring, and in the presence of a base, when X is —O— or —S—, to provide a 7-substituted-4-oxo-1,4-dihydro-3-quinolinecarbonitrile of Formula 3.

3

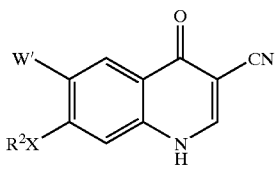

DETAILED DESCRIPTION OF THE INVENTION

The process of the present invention is illustrated in the following reaction schemes. The routes for the preparation of 7-substituted-3-quinolinecarbonitriles of this invention encompassed by Formula (I) is described as follows starting with Scheme 1. 7-Fluoro-4-oxo-1,4-dihydro-3-quinolinecarbonitriles of Formula (II) where W' is —H or —$OR^3$ are converted to 7-fluoro-3-quinolinecarbonitriles 1 wherein Z is a chloro or bromo group by treatment with a halogenating reagent which includes but is not limited to phosphorous oxychloride and phosphorous oxybromide either neat or optionally in the presence of a cosolvent which includes but is not limited to dichloromethane. Reaction of 7-fluoro-3-quinolinecarbonitrile 1 with an amine $R^1NH_2$ 1a wherein $R^1$ is as hereinbefore defined may be carried out in a solvent such as 2-ethoxyethanol in the presence of a catalytic or equivalent amount of pyridine hydrochloride results in the formation of intermediate 7-fluoro-4-(substituted amino)-3-quinolinecarbonitriles 2 where W' is hereinbefore defined. Preferably, amine $R^1NH_2$ 1a is a substituted aniline where $R^1$ is substituted aryl. Displacement of the 7-fluoro group of 7-fluoro-4-(substituted amino)-3-quinolinecarbonitriles 2 with an alkoxide or thioalkoxide anion results in the preparation of 7-substituted-3-quinolinecarbonitriles of Formula (I). This reaction can be performed using an excess of the alcohol $R^2OH$ or thiol $R^2SH$ as the solvent or an optional cosolvent such as N,N-dimethylformamide, dimethyl sulfoxide or N-methylpyrrolidone can be used. The anion can be generated from the alcohol or thiol 2a where X is O or S by the use of a base. Suitable bases include sodium, sodium hydride, potassium and potassium hydride. Preferred bases are sodium and sodium hydride. Commercially available sodium salts of the alcohol or thiol 2a where X is O or S are used if available. Reaction of a compound of the formula $R^2XH$ 2a, where X is —NH—, —$NR^{2'}$— and where $R^{2'}$ and $R^2$ may optionally be taken together with the nitrogen to which they are attached to form a heterocyclic ring, affords 7-substituted-3-quinolinecarbonitriles of Formula (I).

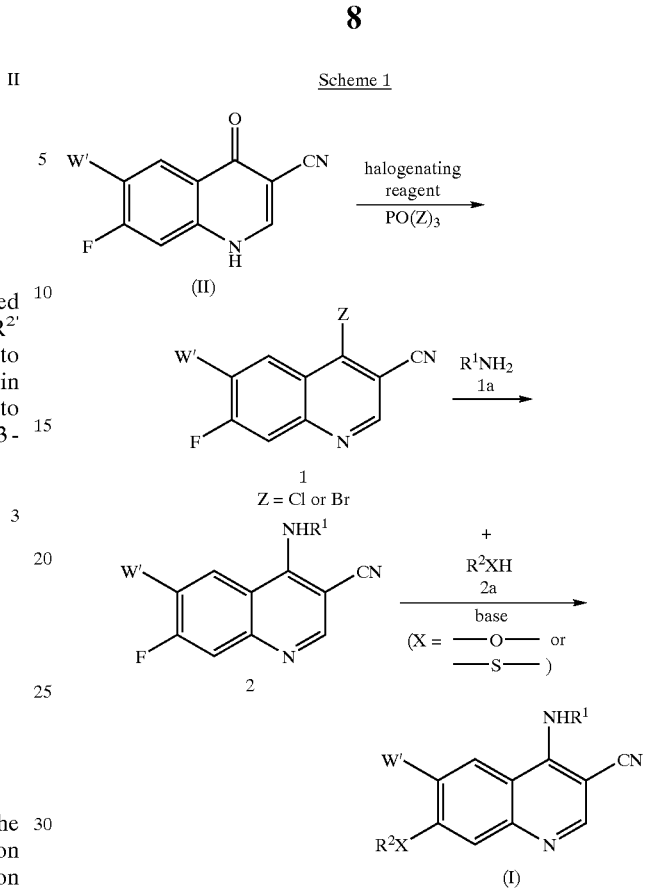

Examples of $R^1$ in the formula herein are 2,4-dichloro-5-methoxyphenyl; cyclopentyl; butyl; 3,4,5-trimethoxyphenyl; 3-chloro-4-(1-methyl-1H-imidazol-2-yl)sulfanyl]phenyl; 2,4-dichorophenyl; 2-chloro-5-methoxyphenyl; 5-methoxy-2-methylphenyl and 2,4-dimethylphenyl.

Examples of $R^2$ in the formulae herein are:2-butynyl; 3-dimethylamino-2,2-dimethylpropyl; 3-(1,1-dioxido-4-thiomorpholinyl)propyl; 2-[2-(1-piperazinyl)ethoxy]ethyl; 2-thienylmethyl;benzyl; ethyl; phenyl; 2-methoxyethyl;pyridin-4-yl; 2-(1-methylpiperidin-4-yl)ethyl; 2-(1-methyl-3-piperidinyl)methyl; 2-(1-methyl-4-piperidinyl)methyl;2-(2-methoxy)ethyl;3-(dimethylamino)propyl; 3-(4-ethyl-1-piperazinyl)propyl ;(1-methylpiperidine-4-yl)methyl; tetrahydro-2H-pyran-2-ylmethyl;3-(1-methylpiperidin-4-yl)propyl;(3-(dimethylamino)propyl)methyl3-(4-methyl)piperazin-1-yl) propyl; 1-methylpiperidin-4-yl)methyl; 1-methylpiperidine-4-yl)methyl; 3-(1-methylpiperidine-4-yl)propyl; 3-(4-methyl-1-piperazinyl)propyl;(1-ethylpiperidine-4-yl) methyl; (1-methylpiperidine-2-yl)methyl; piperidin-4-ylmethyl and 3-(dimethylamino)propyl.

A preferred compound of Formula (I) prepared by the process of the present invention is selected from the group consisting of:

7-(2-Butynyloxy)-4-[(2,4-dichloro-5-methoxyphenyl) amino]-6-methoxy-3-quinolinecarbonitrile;

4-[(2,4-Dichloro-5-methoxyphenyl)amino]-7-(3-dimethylamino-2,2-dimethylpropoxy)-6-methoxy-3-quinolinecarbonitrile;

4-[(2,4-Dichloro-5-methoxyphenyl)amino]-7-[3-(1,1-dioxido-4-thiomorpholinyl)propoxy]-6-methoxy-3-quinolinecarbonitrile;

4-[(2,4-Dichloro-5-methoxyphenyl)amino]-6-methoxy-7-{2-[2-(1-piperazinyl)ethoxy]ethoxy)-3-quinolinecarbonitrile;

4-[(2,4-Dichloro-5-methoxyphenyl)amino]-6-methoxy-7-(2-thienylmethoxy)-3-quinolinecarbonitrile;

7-Benzyloxy-4-[(2,4-dichloro-5-methoxyphenyl)amino]-6-methoxy-3-quinolinecarbonitrile;

4-[(2,4-Dichloro-5-methoxyphenyl)amino]-7-ethylsulfanyl-6-methoxy-3-quinolinecarbonitrile;

4-[(2,4-Dichloro-5-methoxyphenyl)amino]-6-methoxy-7-phenylsulfanyl-3-quinolinecarbonitrile;

4-Cyclopentylamino-6-methoxy-7-(2-methoxyethoxy)-3-quinolinecarbonitrile;

4-Butylamino-6-methoxy-7-(2-methoxyethoxy)-3-quinolinecarbonitrile;

7-Benzylthio-4-[(2,4-dichloro-5-methoxyphenyl)amino]-6-methoxy-3-quinolinecarbonitrile;

4-[(2,4-Dichloro-5-methoxyphenyl)amino]-6-methoxy-7-(pyridin-4-yloxy)-3-quinolinecarbonitrile;

4-[(2,4-Dichloro-5-methoxyphenyl)amino]-6-methoxy-7-[2-(1-methylpiperidin-4-yl)ethoxy]-3-quinolinecarbonitrile;

4-[(2,4-Dichloro-5-methoxyphenyl)amino]-6-methoxy-7-[2-methoxyethoxy]-3-quinolinecarbonitrile;

4-[(2,4-Dichloro-5-methoxyphenyl)amino]-6-methoxy-7-[2-(1-methyl-3-piperidinyl)methoxy]-3-quinolinecarbonitrile;

4-[(2,4-Dichloro-5-methoxyphenyl)amino]-6-methoxy-7-[2-(1-methyl-4-piperidinyl)methoxy]-3-quinolinecarbonitrile;

6-Methoxy-7-[2-methoxyethoxy]-4-[(3,4,5-trimethoxyphenyl)amino]-3-quinolinecarbonitrile;

6-Methoxy-7-[(1-methylpiperidine-4-yl)methoxy]-4-[(3,4,5-trimethoxyphenyl)amino]-3-quinolinecarbonitrile;

4-({3-Chloro-4-[(1-methyl-1H-imidazol-2-yl)sulfanyl]phenyl}amino)-6-methoxy-7-[2-(2-methoxy)ethoxy]-3-quinolinecarbonitrile;

4-({3-Chloro-4-[(1-methyl-1H-imidazol-2-yl)sulfanyl]phenyl}amino)-7-[3-(dimethylamino)propoxy]-6-(2-methoxyethoxy)- 3-quinolinecarbonitrile;

4-({3-Chloro-4-[(1-methyl-1H-imidazol-2-yl)sulfanyl]phenyl}amino)-7-[3-(4-ethyl1-piperazinyl)propoxy]-6-(2-methoxyethoxy)- 3-quinolinecarbonitrile;

4-[(2,4-Dichloro-5-methoxyphenyl)amino]-6-[2-methoxyethoxy]-7-[(1-methylpiperidine-4-yl)methoxy]3-quinolinecarbonitrile;

4-[(2,4-Dichloro-5-methoxyphenyl)amino]-6-ethoxy-7-(2-methoxyethoxy)3-quinolinecarbonitrile;

4-[(2,4-Dichloro-5-methoxyphenyl)amino]-6-methoxy-7-(tetrahydro-2H-pyran-2-ylmethoxy)3-quinolinecarbonitrile;

4-[(2,4-Dichloro-5-methoxyphenyl)amino]-7-(2-methoxyethoxy)-6-(2-morpholin-4-ylethoxy)3-quinolinecarbonitrile;

4-[3-Chloro-4-(1-methyl-1H-imidazol-2-ylsulfanyl)-phenylamino]-6-methoxy-7-(4-methylpiperazin-1-yl)-quinoline-3-carbonitrile;

4-[(2,4-Dichloro-5-methoxyphenyl)amino]-6-methoxy-7-{[3-(1-methylpiperidin-4-yl)propyl]amino}quinoline-3-carbonitrile;

4-[3-Chloro-4-(1-methyl-1H-imidazol-2-ylsulfanyl)-phenylamino]-7-{[3-(dimethyl)aminopropyl]amino}-6-methoxyquinoline-3-carbonitrile;

4-[3-Chloro-4-(1-methyl-1H-imidazol-2-ylsulfanyl)-phenylamino]-7-{[3-(dimethylamino)propyl]-methylamino}-6-methoxyquinoline-3-carbonitrile;

4-[(2,4-Dichloro-5-methoxyphenyl)amino]-7-[3-(4-methyl)piperazin-1-yl)propoxy]-3-quinolinecarbonitrile;

4-[(2,4-Dichloro-5-methoxyphenyl)amino]-7-[(1-methylpiperidin-4-yl)methoxy]-3-quinolinecarbonitrile;

4-[(2,4-Dichloro-5-methoxyphenyl)amino]-7-(2-methoxyethoxy)-3-quinolinecarbonitrile;

4-[(2,4-Dichorophenyl)amino]-6-methoxy-7-(2-methoxyethoxy)quinoline-3-carbonitrile;

4-[(2,4-Dimethyl-5-methoxyphenyl)amino]-6-methoxy-7-(2-methoxyethoxy)quinoline-3-carbonitrile;

4-[(2-Chloro-5-methoxyphenyl)amino]-6-methoxy-7-(2-methoxyethoxy)quinoline-3-carbonitrile;

6-Methoxy-7-(2-methoxyethoxy)-4-[(5-methoxy-2-methylphenyl)amino]-quinoline-3-carbonitrile;

4-[(2,4-Dimethylphenyl)amino]-6-methoxy-7-(2-methoxyethoxy)quinoline-3-carbonitrile;

4-[(2,4-Dichlorophenyl)amino]-6-methoxy-7-[(1-methylpiperidine-4-yl)methoxy]quinoline-3-carbonitrile;

4-[(2,4-Dimethyl-5-methoxyphenyl)amino]-6-methoxy-7-[(1-methylpiperidine-4-yl)methoxy]quinoline-3-carbonitrile;

6-Methoxy-4-[(5-methoxy-2-methylphenyl)amino]-7-[(1-methylpiperidine-4-yl)methoxy]quinoline-3-carbonitrile;

4-[(2-Chloro-5-methoxyphenyl)amino]-6-methoxy-7-[(1-methylpiperidine-4-yl)methoxy]quinoline-3-carbonitrile;

4-[(2,4-Dimethylphenyl)amino]-6-methoxy-7-[(1-methylpiperidine-4-yl)methoxy]quinoline-3-carbonitrile;

4-[(2,4-Dichloro-5-methoxyphenyl)amino]-6-methoxy-7-[3-( 1-methylpiperidine-4-yl)propoxy]quinoline-3-carbonitrile;

4-[(2-Chloro-5-methoxyphenyl)amino]-6-methoxy-7-[3-(1-methylpiperidine-4-yl)propoxy]quinoline-3-carbonitrile;

6-Methoxy-4-[(5-methoxy-2-methylphenyl)amino]-7-[3-(1-methylpiperidine-4-yl)propoxy]quinoline-3-carbonitrile;

4-[(2,4-Dimethylphenyl)amino]-6-methoxy-7-[3(1-methylpiperidine-4-yl)propoxy]quinoline-3-carbonitrile;

4-[(2,4-Dichloro-5-methoxyphenyl)amino]-6-methoxy-7-[3-(4-methyl-1-piperazinyl)propoxy]quinoline-3-carbonitrile;

4-[(2,4-Dichloro-5-methoxyphenyl)amino]-7-[(1-ethylpiperidine-4-yl)methoxy]-6-methoxyquinoline-3-carbonitrile;

4-[(2,4-Dichloro-5-methoxyphenyl)amino]-6-methoxy-7-[(1-methylpiperidine-2-yl)methoxy]quinoline-3-carbonitrile;

4-[(2,4-Dichloro-5-methoxyphenyl)amino]-6-methoxy-7-(piperidin-4-ylmethoxy)quinoline-3-carbonitrile;

4-[(2,4-Dichloro-5-methoxyphenyl)amino]-7-{[3-(dimethylamino)propyl]amino}-6-methoxyquinoline-3-carbonitrile;

4-[(2,4-Dichloro-5-methoxyphenyl)amino]-7-{[3-(dimethylamino)propyl](methyl)amino]-6-methoxyquinoline-3-carbonitrile; and 4-[(2,4-Dichloro-5-methoxyphenyl)amino]-6-methoxy-7-[(2-methoxyethyl)amino]quinoline-3-carbonitrile.

An alternative route to 7-substituted-3-quinolinecarbonitriles of Formula (I) is described in Scheme 2. 7-Fluoro-4-oxo-1,4-dihydro-3-quinolinecarbonitriles of Formula (II) where W' is hereinbefore defined are converted to 7-substituted-4-oxo-1,4-dihydro-3-quinolinecarbonitriles 3 by replacement of the 7-fluoro group with an alkoxide or thioalkoxide anion. This reaction can be performed using an excess of the alcohol or thiol as the solvent or optionally a cosolvent such as N,N-dimethylformamide, dimethyl sulfoxide or N-methylpyrrolidone may be used. The anion may be generated from the alcohol or thiol 2a where X is O or S respectively by the use of a base. Suitable bases include sodium, sodium hydride, potassium and potassium hydride. Preferred bases are sodium and sodium hydride. Commercially available sodium salts of the alcohol or thiol 2a where X is O or S are used if available. Reaction of 7-fluoro-4-oxo-1,4-dihydro-3-quinolinecarbonitriles of Formula (II) with a compound of the formula $R^2XH$ 2a, where X is —NH—, —$NR^{2'}$— and where $R^{2'}$ and $R^2$ may optionally be taken together with the nitrogen to which they are attached to form a heterocyclic ring, to afford 7-substituted-4-oxo-1,4-dihydro-3-quinolinecarbonitriles 3. Treatment of 7-substituted-4-oxo-1,4-dihydro-3-quinolinecarbonitriles 3 with a halogenating reagent $PO(Z)_3$ wherein Z is a chloro or bromo group which include but not limited to phosphorous oxychloride, phosphorous oxybromide either neat or optionally in the presence of a cosolvent which include but not limited to dichloromethane affords 7-substituted-4-halo-3-quinolinecarbonitriles 4 which are further reacted with an amine 1a wherein $R^1$ is as hereinbefore defined in a solvent such as 2-ethoxyethanol in the presence of a catalytic or equivalent amount of pyridine hydrochloride results in the formation of 7-substituted-3-quinolinecarbonitriles of Formula (I). Preferably amine $R^1NH_2$ 1a is a substituted aniline where $R^1$ is substituted aryl.

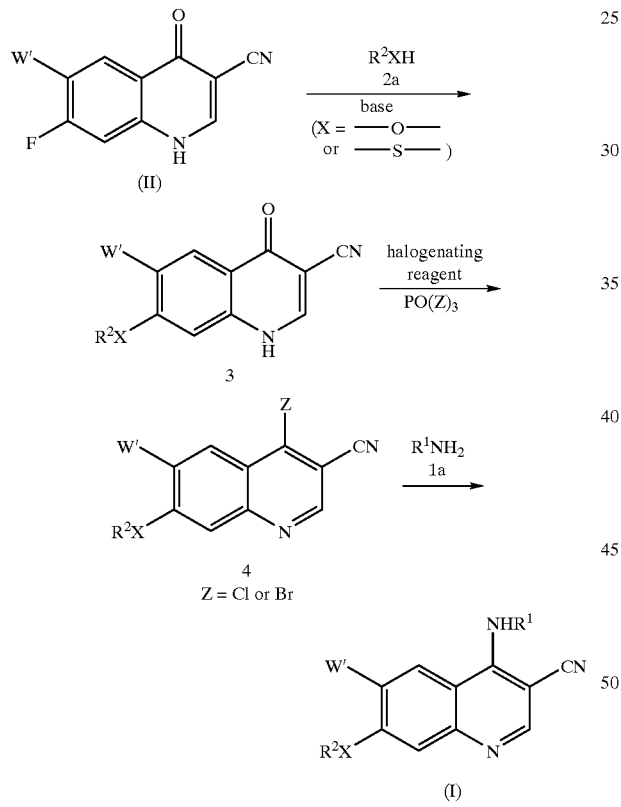

Scheme 2

A preferred compound of formula (I) prepared by the process of the present invention is:

4-[(2,4-Dichlorophenyl)amino]-7-(2-methoxyethoxy) quinoline-3-carbonitrile;

6-Butoxy-4-[(2,4-dichloro-5-methoxyphenyl)amino]-7-(2-methoxyethoxy)-3-quinolinecarbonitrile;
6-Methoxy-7-(4-methylpiperazin-1-yl)-4-(4-phenoxyphenylamino)-quinoline-3-carbonitrile; and
6-Methoxy-7-(1-methyl-piperidin-4-ylmethoxy)-4-{[4-(pyridin-3-yloxy)-phenyl]amino}quinoline-3-carbonitrile A preferred compound of formula 3 prepared by the process of the present invention is selected from the group consisting of:

6-Methoxy-7-(2-methoxyethoxy)-4-oxo-1,4,-dihydro-3-quinolinecarbonitrile;
6-Methoxy-7-(4-methyl-piperazin-1-yl)-4-oxo-1,4-dihydroquinoline-3-carbonitrile; and
7-(2-Methoxyethoxy)-4-oxo-1,4-dihydroquinoline-3-carbonitrile.

An alternative approach, as shown in Scheme 3, for the preparation of 7-substituted-3-quinolinecarbonitriles of Formula (I) uses a protecting group of the hydroxy group at C-6 of the 3-quinolinecarbonitrile 5. The protecting group is designated $R^{3'}$ and includes but is not limited to groups including benzyl and isopropyl which may be removed to provide the 6-hydroxy derivative 6. Specifically, if $R^{3'}$ is a benzyl protecting group, the desired hydroxy group can be obtained by treatment with trifluoroacetic acid in the presence of thioanisole. Further, if $R^{3'}$ is an isopropyl protecting group, the desired 6-hydroxy derivative 6 may be obtained by treatment with aluminum trichloride. Further reaction of 6-hydroxy derivative 6 with an alcohol $R^3OH$ 6a in the presence of triphenyl phosphine ($Ph_3P$) where Ph is phenyl and diethylazodicarboxylate (DEAD), in a solvent such as tetrahydrofuran affords 4-halo-3-quinolinecarbonitriles 7.

Scheme 3

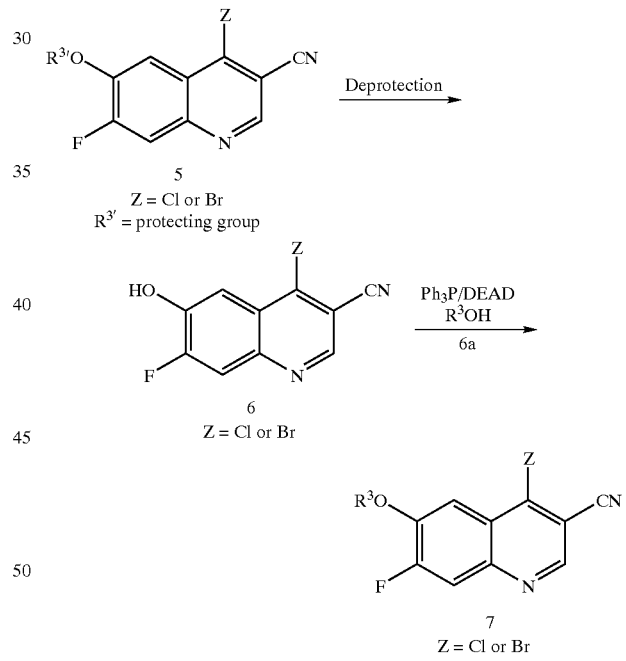

Additional intermediates may be prepared as shown in Scheme 4 where 4-halo-3-quinolinecarbonitriles 8 with $R^2$ and $R^{3'}$ as hereinbefore defined are deprotected to afford 6-hydroxyquinolines 9 using conditions as defined for deprotection in Scheme 3. Further reaction of 6-hydroxy derivatives 9 with an alcohol $R^3OH$ 6a in the presence of triphenyl phosphine ($Ph_3P$) where Ph is phenyl, and diethylazodicarboxylate (DEAD), in a solvent such as tetrahydrofuran affords 4-halo-3-quinolinecarbonitriles 10 which may be further reacted with an amine $R^1NH_2$ 1a to afford 7-substituted-3-quinolinecarbonitriles 11. Preferably amine $R^1NH_2$ 1a is a substituted aniline where $R^1$ is substituted aryl.

Scheme 4

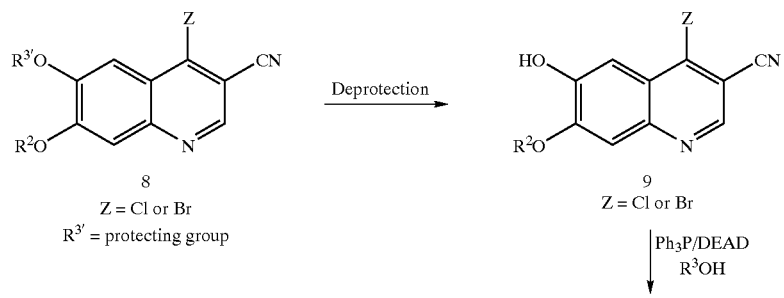

The 7-substituted-4-oxo-1,4-dihydro-3-quinolinecarbonitriles 3 and 7-substituted-4-halo-3-quinolinecarbonitriles 4 are key intermediates used to prepare 7-substituted-3-quinolinecarbonitriles of Formula (I). Scheme 5 shows two alternate routes for the preparation of additional key intermediates, 7-fluoro-4-oxo-1,4-dihydro-3-quinolinecarbonitriles of Formula (II). Anilines 12 may be treated with ethyl (ethoxymethylene)cyanoacetate either neat or optionally in the presence of a cosolvent such as toluene, at temperatures ranging from about 60 to about 120° C. followed by subsequent thermal cyclization, preferably in a eutectic solvent system which includes a 3:1 mixture of diphenyl ether (Ph-O-Ph) and biphenyl(Ph—Ph) at a temperature range of about 240° to about 260°, affords 7-fluoro-4-oxo-1,4-dihydro-3-quinolinecarbonitriles of Formula (II). Alternatively, aniline 12 is reacted with diethyl (ethoxymethylene)malonate either neat or optionally in the presence of a cosolvent toluene, at temperatures ranging from about 60 to about 120° C. Subsequent thermal cyclization, preferably in a eutectic solvent system which includes 3:1 mixture of diphenyl ether and biphenyl at elevated temperature, at a temperature range of about 240° to about 260° C., provides ester 13. Hydrolysis of the ester 13 under preferably basic conditions, such as sodium hydroxide in an alcoholic solvent such as ethanol, at reflux temperatures results in carboxylic acid 14. Conversion of carboxylic acid 14 to primary amide 15 may be accomplished by treatment with an activating agent which includes N,N-carbonyl diimidazole(CDI) or oxalyl chloride followed by the addition of either ammonia gas or preferably an aqueous solution of ammonium hydroxide. Dehydration of primary amide 15 with a reagent such as cyanuric chloride in a solvent such as N,N-dimethylformamide provides 7-fluoro-4-oxo-1,4-dihydro-3-quinolinecarbonitriles of Formula (II).

Scheme 5

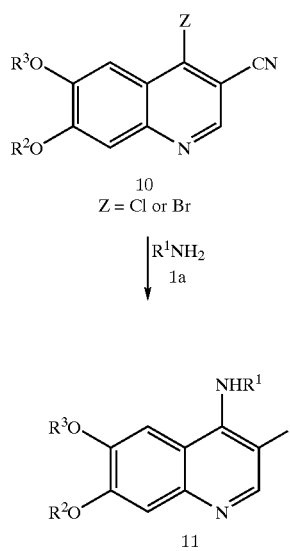

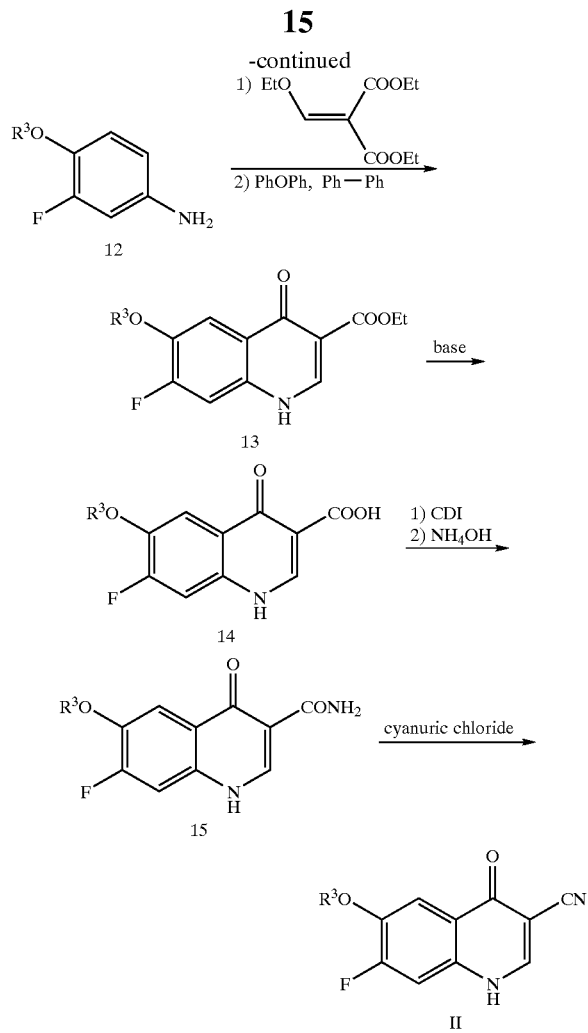

Alternatively compounds of Formula (II) may be prepared as shown in Scheme 6 from the corresponding anthranilic acid or ester 16 where $R^{10}$ is H or alkyl of 1 to 6 carbon atoms by reaction with N,N-dimethylformamide dimethyl acetal or preferably with N,N-dimethylformamide diethylacetal, optionally in the presence of a cosolvent toluene at about 100–130° C. to provide amidine 17. Reaction of the anion of acetonitrile, preferably generated from the reaction of n-butyl lithium with acetonitrile, in an inert solvent such as tetrahydrofuran at about −78° C., with amidine 17 provides compounds of Formula (II).

Scheme 6

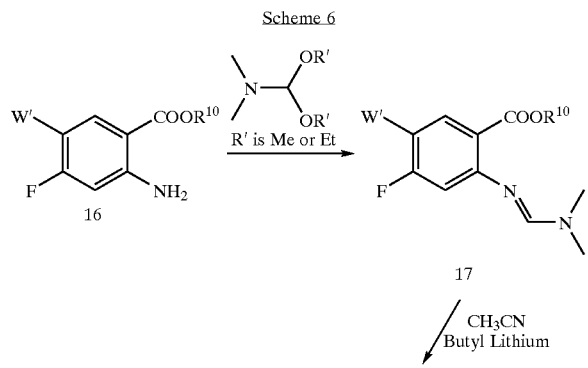

The compounds of this invention are prepared from: (a) commercially available starting materials (b) known starting materials which can be prepared as described in literature procedures or (c) new intermediates described in the schemes and experimental procedures herein.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art. Reactions are run under inert atmospheres where appropriate.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic and similarly known acceptable acids.

Alkyl as used herein means a branched or straight chain radical having from 1 to 6 carbon atoms optionally substituted.

Alkenyl as used herein means a branched or straight chain radical having 2 to 6 carbon atoms optionally substituted. The chain having at least one double bond.

Alkynyl as used herein means a branched or straight chain radical having from 2 to 6 carbon atoms optionally substituted. The chain having at least one triple bond.

Alkoxy as used herein means an alkyl-O— group in which the alkyl group is as previously described. Exemplary alkoxy groups include but are not limited to methoxy, ethoxy, n-propoxy, i-propoxy, n-butoxy, and t-butoxy.

Cycloalkyl as used herein means a saturated ring system having from 3 to 10 carbon atoms. Preferred is 3 or 7 carbon atoms. Exemplary cycloalkyl rings include but are not limited to cyclopropyl, cyclobutyl, cyclopentyl, cyclohexyl, and the like.

Aryl as used herein means a mono or bicyclic aromatic ring having from 6 to 12 carbon atoms. Monocyclic rings preferably have 6 members and bicyclic rings preferably have 8, 9, 10 or 12 membered ring structures. Exemplary aryl groups include phenyl, alpha-naphthyl, beta-naphthyl, indene, and the like independently substituted with one or more substituents and more preferably with 1 to 4 substituents.

Heteroaryl denotes an unsubstituted or optionally substituted monocyclic 5 or 6 membered ring, which contains 1 to 4, or particularly 1 or 2 heteroatoms which may be the same or different. Nitrogen, oxygen and sulfur are the preferred heteroatoms, provided that the heteroaryl does not contain O—O, S—S or S—O bonds. Specific examples include thiophene, furan, pyrrole, pyrazole, imidazole, 1,2,3-triazole, 1,2,4-triazole, tetrazole, thiazole, oxazole, isothiazole, isoxazole, 1,3,4-oxadiazole, 1,2,4-oxadiazole, 1,3,4-thiadiazole, pyridine, pyrimidine, pyrazine, pyridazine and 1,3,5-triazine. The heteroaryl ring may be oxidized when a heteroatom is a nitrogen atom to provide the corresponding N-oxide, including pyridine —N-oxide or the heterocyclic ring may contain a carbonyl group on one of the carbon atoms, such as 1,3,4-oxadiazol-2-one.

Bicyclic heteroaryl as used herein refers to saturated or partially unsaturated bicyclic fused rings having 8 to 20 ring atoms containing 1 to 4 heteroatoms which may be the same or different independently selected from nitrogen, oxygen and sulfur optionally substituted with 1 to 3 independently selected substituents which may be the same or different provided that the bicyclic heteroaryl does not contain O—O, S—S or S—O bonds. Specific examples include: indole, 2,3-dihydroindole, 2-indazole, isoindazole, quinoline, isoquinoline, tetrahydroquinoline, benzofuran, benzothiophene, benzimidazole, benzotriazole, benzothiazole, benzoxazole, benzisoxazole, 1,2-benzopyran, cinnoline, phthalazine, quinazoline, 1,8-naphthyridine, pyrido[3,2-b]pyridine, pyrido[3,4-b]pyridine, pyrido[4,3-b]pyridine, pyrido[2,3-d]pyrimidine, purine, and pteridine and the like. Either or both rings of the bicyclic ring system may be partially saturated, or fully saturated, and the bicyclic group may be oxidized on a nitrogen atom to provide the corresponding N-oxide, such as quinoline —N-oxide, or the bicyclic ring system may contain a carbonyl group on one of the carbon atoms, such as 2-indanone.

Heterocyclyl, heterocyclyl group or heterocyclic ring means a saturated or partially unsaturated monocyclic radical containing preferably 3 to 8 ring atoms, more preferably 3 to 7 ring atoms and most preferably 5 to 6 ring atoms selected from carbon, nitrogen, oxygen and sulfur with at least 1 and preferably 1 to 4, more preferably 1 to 2 nitrogen, oxygen or sulfur as ring atoms. Specific examples include but are not limited to morpholine, thiomorpholine, thiomorpholine-S-oxide, thiomorpholine-S,S-dioxide, piperidine, N-alkylpiperidine, piperazine, N-alkylpiperazine, pyrrolidine, aziridine, oxirane, tetrahydrothiophene, tetrahydrofuran, 1,2-pyran, 1,4-pyran, dioxane, 1,3-dioxolane and tetrahydropyran. The heterocyclyl ring may be oxidized on a tri-substituted nitrogen atom to provide the corresponding N-oxide, such as N-ethylpiperazine-N-oxide, or the heterocyclyl ring may contain a carbonyl group on one of the carbon atoms, such as pyrrolidinone. In order to facilitate a further understanding of the invention, the following non-limiting examples illustrate the process of the present invention.

Reference Example 1

Ethyl 7-fluoro-6-methoxy-4-oxo-1,4-dihydro-3-quinolinecarboxylate

A mixture of 3-fluoro-4-methoxyaniline (3.00 g, 21.26 mmol) and diethyl ethoxymethylene malonate (4.59 g, 21.26 mmol) is heated at 110° C. for 1 hour then cooled to room temperature. Hexane is added and the solids collected by filtration. This material is suspended in 45 mL of a 3:1 mixture of diphenyl ether:biphenyl and the mixture is heated at reflux for 2 hours to provide a brown solution. The reaction mixture is cooled to room temperature and hexane is added. The resultant solid is collected by filtration washing with hexane to provide 2.62 g of ethyl 7-fluoro-6-methoxy-4-oxo-1,4-dihydro-3-quinolinecarboxylate as a white solid, mp>300° C.

MS 265.9 (M+H)+ Analysis for $C_{13}H_{12}FNO_4$ Calcd: C, 58.87; H, 4.56; N, 5.28. Found: C, 58.66; H, 4.16; N, 5.14.

Reference Example 2

7-Fluoro-6-methoxy-4-oxo-1,4-dihydro-3-quinolinecarboxylic acid

A mixture of ethyl 7-fluoro-6-methoxy-4-oxo-1,4-dihydro-3-quinolinecarboxylate (2.2 g, 8.30 mmol) and 13.2 mL of 1 N sodium hydroxide and 40 mL of ethanol is heated at reflux for 3 hours then cooled to room temperature. Water is added and the mixture is acidified with acetic acid. The resultant solid is collected by filtration washing with water to provide 1.90 g of 7-fluoro-6-methoxy-4-oxo-1,4,-dihydro-3-quinolinecarboxylic acid as a white solid, mp 265–267° C.

MS 238.1 (M+H)+ Analysis for $C_{11}H_8FNO_4$-1.2 $H_2O$ Calcd: C, 51.04; H, 4.03; N, 5.41. Found: C, 50.98; H, 3.95; N, 5.33.

Reference Example 3

7-Fluoro-6-methoxy-4-oxo-1,4-dihydro-3-quinolinecarboxamide

A mixture of 7-fluoro-6-methoxy-4-oxo-1,4-dihydro-3-quinolinecarboxylic acid (1.0 g, 4.21 mmol) and N,N'-carbonyldiimidazole (1.51 g, 9.28 mmol) in 14 mL of N,N-dimethylformamide is heated at 65° C. for 2 hours then cooled to room temperature and poured into 200 mL of aqueous ammonium hydroxide in an ice water bath. The solution is allowed to stir at room temperature overnight and then concentrated to a small volume. Ice cold water is added followed by acidification with acetic acid. The resultant solid is collected by filtration washing with water to provide 821 mg of 7-fluoro-6-methoxy-4-oxo-1,4-dihydro-3-quinolinecarboxamide as a white solid, mp>300° C.

MS 236.8 (M+H)+ Analysis for $C_{11}H_9FN_2O_3$-0.2 $H_2O$ Calcd: C, 55.09; H, 3.94; N, 11.68. Found: C, 55.00; H, 3.63; N, 11.49.

Reference Example 4

7-Fluoro-6-methoxy-4-oxo-1,4-dihydro-3-quinolinecarbonitrile

A mixture of 7-fluoro-6-methoxy-4-oxo-1,4,-dihydro-3-quinolinecarboxamide (700 mg, 3.0 mmol) and cyanuric chloride (341 mg, 1.65 mmol) in 15 mL of N,N,-dimethylformamide is heated at 65° C. for 6 hours then cooled to room temperature and an additional 206 mg of cyanuric chloride is added. The mixture is heated at 65° C. for 4 hours then stirred overnight at room temperature. The reaction mixture is poured into ice water and neutralized with saturated sodium bicarbonate. The solids are collected by filtration washing with water and hexane to provide 610 mg of crude product. Purification by flash column chromatography eluting with a gradient of 3% methanol in dichloromethane to 10% methanol in dichloromethane, provides 272 mg of 7-fluoro-6-methoxy-4-oxo-1,4-dihydro-3-quinolinecarbonitrile, mp 147–149° C.

MS 216.8 (M−H)− Analysis for $C_{11}H_7FN_2O_2$-0.1 dichloromethane Calcd: C, 58.80; H, 3.19; N, 12.36.Found: C, 59.06; H, 2.96; N, 11.97.

Reference Example 4

Alternate Preparation of 7-Fluoro-6-methoxy-4-oxo-1,4-dihydro-3-quinolinecarbonitrile A mixture of 3-fluoro-4-methoxyaniline (15.31 g, 108 mmol) and ethyl (ethoxymethylene)cyanoacetate (18.36 g, 108 mmol) in toluene is heated at 100–110° C. for 4.5 hours then cooled to room temperature. A 1:1 mixture of hexane and ethyl acetate is added and the mixture is cooled on an ice bath. The solids are collected washing with hexane to provide a first crop of 26.10 g and a second crop of 1.24 g. A 2.0 g portion of this material is added to 18 mL of a 3:1 mixture of diphenyl ether:biphenyl that is heated to reflux. This mixture is heated at reflux for 4 hours then cooled and poured into hexane. The solids are collected by filtration and washed with ethyl acetate and hexane to provide 624 mg of 7-fluoro-6-methoxy-4-oxo-1,4,-dihydro-3-quinolinecarbonitrile as a brown solid. The filtrate is concentrated, the residue is dissolved in ethyl acetate and hexane is added. The resultant solid is collected by filtration to give 1.07 g of 7-fluoro-6-methoxy-4-oxo-1,4-dihydro-3-quinolinecarbonitrile as a yellow solid.

Reference Example 5

4-Chloro-7-fluoro-6-methoxy-3-quinolinecarbonitrile

A mixture of 7-fluoro-6-methoxy-4-oxo-1,4-dihydro-3-quinolinecarbonitrile (1.0 g, 4.59 mmol) and 14 g of phosphorous oxychloride is heated at reflux for 30 minutes then concentrated in vacuo. The residue is partitioned between aqueous sodium bicarbonate and ethyl acetate. The organic layer is dried over magnesium sulfate, filtered and concentrated on to silica gel. Purification by flash column chromatography eluting with a gradient of 1:5 ethyl acetate:hexane to 1:1 ethyl acetate:hexane, provides 631 mg of 4-chloro-7-fluoro-6-methoxy-3-quinolinecarbonitrile, mp 160–162° C.

MS 236.9 (M+H)+ Analysis for $C_{11}H_6ClFN_2O$ Calcd: C, 55.83; H, 2.56; N, 11.84. Found: C, 55.66; H, 2.84; N, 11.91.

Reference Example 6

6-Methoxy-7-(2-methoxyethoxy)-4-oxo-1,4,-dihydro-3-quinolinecarbonitrile

Sodium (84 mg, 3.67 mmol) is added to 3.6 mL of 2-methoxyethanol and the mixture is heated at reflux for 90 minutes. 7-Fluoro-6-methoxy-4-oxo-1,4,-dihydro-3-quinolinecarbonitrile (200 mg, 0.92 mmol) is added and the reaction mixture is heated at reflux for 4 hours then stirred at room temperature overnight. The reaction mixture is poured into ice water and acidified with acetic acid. The solids are collected by filtration, washing with ethyl acetate and hexane, to provide 234 mg of 6-methoxy-7-(2-methoxyethoxy)-4-oxo-1,4,-dihydro-3-quinolinecarbonitrile, mp>300° C.

MS 272.9 (M−H)− Analysis for $C_{14}H_{14}N_2O_4$-0.15 ethyl acetate Calcd: C, 60.99; H, 5.31; N, 9.75. Found: C, 61.12; H, 5.29; N, 9.49.

Reference Example 7

4-Chloro-6-methoxy-7-(2-methoxyethoxy)-3-quinolinecarbonitrile

A mixture of 6-methoxy-7-(2-methoxyethoxy)-4-oxo-1,4,-dihydro-3-quinolinecarbonitrile (180 mg, 0.66 mmol) and 2.02 g of phosphorous oxychloride is heated at reflux for 40 minutes then concentrated in vacuo. The residue is added to water and the pH is adjusted to 8 by the addition of aqueous sodium bicarbonate. The solids are collected by filtration, washing with water and hexane, to provide 169 mg of 4-chloro-6-methoxy-7-(2-methoxyethoxy)-3-quinolinecarbonitrile, mp 178–180° C.

MS 292.9 (M+H)+ Analysis for $C_{14}H_{14}N_2O_4$-0.60 $H_2O$ Calcd: C, 55.39; H, 4.70; N, 9.23. Found: C, 55.23; H, 4.30; N, 8.87.

Reference Example 8

4-[(2,4-Dichloro-5-methoxyphenyl)amino]-7-fluoro-6-methoxy-3-quinolinecarbonitrile A mixture of 4-chloro-7-fluoro-6-methoxy-3-quinolinecarbonitrile (4.12 g, 18 mmol) 2,4-dichloro-5-methoxyaniline (4.56 g, 24 mmol) (Theodoridis, G.; Pestic. Sci. 1990, 30, 259) and pyridine hydrochloride (2.31 g, 19.9 mmol) in 45 mL of 2-ethoxyethanol is heated at 120° C. for 3 hours then cooled to room temperature. The reaction mixture is added to aqueous sodium bicarbonate and stirred for 20 minutes. The solids are collected by filtration to provide 4.89 g of 4-[(2,4-dichloro-5-methoxyphenyl)amino]-7-fluoro-6-methoxy-3-quinolinecarbonitrile, mp>260° C.

HRMS theory 392.03634; found 392.03556 (M+H)+ Analysis for $C_{18}H_{12}Cl_2FN_3O_2$-2.0 $H_2O$ Calcd: C, 50.48; H, 3.77; N, 9.81. Found: C, 50.41; H, 2.82; N, 9.78.

Reference Example 9

4-Cyclopentylamino-7-fluoro-6-methoxy-3-quinolinecarbonitrile

A mixture of 4-chloro-7-fluoro-6-methoxy-3-quinolinecarbonitrile (400 mg, 1.69 mmol) and cyclopentylamine (307 mg, 3.72 mmol) in 11 mL of 2-ethoxyethanol is heated at 100° C. for 1.5 hours then cooled to room temperature. The reaction mixture is concentrated in vacuo and aqueous sodium bicarbonate is added to the residue. After stirring for 20 minutes, the solids are collected by filtration. Purification by preparative thin layer chromatography, eluting with 5% methanol in dichloromethane, followed by trituration with diethyl ether and hexane, provides 359 mg of 4-cyclopentylamino-7-fluoro-6-methoxy-3-quinolinecarbonitrile, mp 162–164° C.

MS 286.13 (M+H)+ Analysis for $C_{16}H_{16}FN_3O$-0.25 $H_2O$ Calcd: C, 66.31; H, 5.74; N, 14.50. Found: C, 66.38; H, 5.80; N, 14.45.

Reference Example 10

4-Butylamino-7-fluoro-6-methoxy-3-quinolinecarbonitrile

A mixture of 4-chloro-7-fluoro-6-methoxy-3-quinolinecarbonitrile (300 mg, 1.27 mmol) and butylamine (205 mg, 2.80 mmol) in 10 mL of 2-ethoxyethanol is heated at 80° C. for 1.5 hours then cooled to room temperature. The reaction mixture is concentrated in vacuo and aqueous sodium bicarbonate is added to the residue. After stirring for 20 minutes, the solids are collected by filtration. Purification by preparative thin layer chromatography, eluting with 2% methanol in dichloromethane provides 230 mg of 4-butylamino-7-fluoro-6-methoxy-3-quinolinecarbonitrile, mp 155–156° C.

MS 274.2 (M+H)+ Analysis for $C_{15}H_{16}FN_3O$-0.2 $H_2O$ Calcd: C, 65.06; H, 5.98; N, 15.17. Found: C, 65.02; H, 5.91; N, 15.03.

Reference Example 11

6-Benzyloxy-7-fluoro 4-oxo-1, 4-dihydro-3-quinolinecarbonitrile

A mixture of 4-benzyloxy-3-fluoroaniline (6.06 g, 27.9 mmol) (U.S. Pat. No. 5,622,967) and ethyl (ethoxymethylene)cyanoacetate (5.08 g, 30.0 mmol) is heated at 120° C. for 45 minutes then cooled to room temperature. This solid is added in portions to a 3:1 mixture of diphenyl ether:biphenyl at 245° C. This mixture is heated at 245° C. for 3 hours then cooled and the solids are collected by filtration, washing with hexane and diethyl ether to provides 2.60 g of 6-benzyloxy-7-fluoro-4-oxo-1, 4-dihydro-3-quinolinecarbonitrile, mp>250° C.

MS 293.1 (M−H)−

Reference Example 12

6-Benzyloxy-4-chloro-7-fluoro-3-quinolinecarbonitrile

A mixture of 7-fluoro-6-methoxy-4-oxo-1, 4-dihydro-3-quinolinecarbonitrile (645 mg, 2.19 mmol) and 10 mL of phosphorous oxychloride is heated at 115° C. for 1.5 hours then concentrated in vacuo. The residue is treated with ice cold aqueous ammonium hydroxide and the resultant solid is collected by filtration. Purification by flash column chromatography eluting with a gradient of 1% ethyl acetate in hexane to 6% ethyl acetate in hexane, provides 284 mg of 6-benzyloxy-4-chloro-7-fluoro-3-quinolinecarbonitrile, mp 159–160° C.

MS 313.13 (M+H)+ Analysis for $C_{17}H_{10}ClFN_2O$ Calcd: C, 65.15; H, 3.06; N, 8.82. Found: C, 65.29; H, 3.22; N, 8.96.

Reference Example 13

4-Chloro-7-fluoro-6-hydroxy-3-quinolinecarbonitrile

A mixture of 6-benzyloxy-4-chloro-7-fluoro-3-quinolinecarbonitrile (733 mg, 2.34 mmol) and 1 mL of thioanisole in 12 mL of trifluoroacetic acid is heated at reflux for 9 hours then concentrated in vacuo. The residue is treated with ice water and then basified to pH 9–10 by the addition of aqueous ammonium hydroxide. The resultant solid is collected by filtration and washed with diethyl ether. The filtrate is extracted with 10% methanol in ethyl acetate. The organic layer is dried over sodium sulfate, filtered and concentrated in vacuo. The residue is combined with the solid obtained initially, and this material is dissolved in 5% methanol in ethyl acetate and absorbed onto silica gel. Purification by flash column chromatography eluting with a gradient of hexane to increasing amounts of ethyl acetate in hexane to 5% methanol in ethyl acetate provides 260 mg of 4-chloro-7-fluoro-6-hydroxy-3-quinolinecarbonitrile, mp>250° C.

MS 220.9 (M−H)− Analysis for $C_{10}H_4ClFN_2O$ Calcd: C, 53.96; H, 1.81; N, 12.58. Found: C, 54.23; H, 2.02; N, 12.06.

Reference Example 14

4-Chloro-6-ethoxy-7-fluoro-3-quinolinecarbonitrile

To a 0° C. mixture of 4-chloro-7-fluoro-6-hydroxy-3-quinolinecarbonitrile (185 mg, 0.83 mmol), triphenylphosphine (392 mg, 1.49 mmol) and ethanol (153 mg, 3.32 mmol) in 15 mL of tetrahydrofuran is added diethylazodicarboxylate (260 mg, 1.80 mmol). The reaction mixture is kept at 0° C. for 45 minutes then stirred at room temperature overnight. The reaction mixture is concentrated in vacuo and purified by flash column chromatography eluting with a gradient of 1 % ethyl acetate in hexane to 5% ethyl acetate in hexane provides 4-chloro-6-ethoxy-7-fluoro-3-quinolinecarbonitrile, mp 165–166° C.

MS 251.0 (M+H)+ Analysis for $C_{12}H_8ClFN_2O$ Calcd: C, 57.50; H, 3.22; N, 11.18. Found: C, 57.24; H, 3.41; N, 11.09.

Reference Example 15

7-Fluoro-6-methoxy-4-[(3,4,5-trimethoxyphenyl)amino]-3-quinolinecarbonitrile

A mixture of 4-chloro-7-fluoro-6-methoxy-3-quinolinecarbonitrile (500 mg, 2.11 mmol), 3,4,5-trimethoxyaniline (515 mg, 2.81 mmol) and pyridine hydrochloride (270 mg , 2.33 mmol) in 20 mL of 2-ethoxyethanol is heated at reflux for 4 hours then cooled to room temperature. The reaction mixture is poured into aqueous sodium bicarbonate and stirred at room temperature for 15 minutes. The solid is collected by filtration and partitioned between water and ethyl acetate. The organic layer is dried over magnesium sulfate, filtered and concentrated in vacuo. Trituration of the residue with ethyl acetate and diethyl ether provides 512 mg of 7-fluoro-6-methoxy-4-[(3,4,5-trimethoxyphenyl)amino]-3-quinolinecarbonitrile, mp 215–217° C.

MS 384.10 (M+H)+ Analysis for $C_{20}H_{18}Cl_2FN_3O_4$-0.8 $H_2O$ Calcd: C, 60.39; H, 4.97; N, 10.56. Found: C, 60.75; H, 4.86; N, 10.16.

Reference Example 16

2-Fluoro-1-(2-methoxyethoxy)-4-nitrobenzene

A mixture of 2-fluoro-5-nitrophenol (10.0 g , 63.7 mmol), 2-bromoethyl methyl ether (15.0 g, 107.9 mmol) and potassium carbonate (26.5 g, 192 mmol) in 40 mL of N, N'-dimethylformamide is heated at 70° C. for 4 hours then cooled to room temperature and poured onto ice. The solid is collected by filtration washed with water and dried to provide 12.0 g of 2-fluoro-1-(2-methoxyethoxy)-4-nitrobenzene, mp 62–63° C.

MS 216.02 (M+H)+ Analysis for $C_9H_{10}FNO_4$ Calcd: C, 50.24; H, 4.68; N, 6.51. Found: C, 50.24; H, 4.67; N, 6.49.

Reference Example 17

3-Fluoro-4-(2-methoxyethoxy)aniline

A mixture of 2-fluoro-1-(2-methoxyethoxy)-4-nitrobenzene (12.0 g , 55.7 mmol), iron powder (10.3 g, 180 mmol) and ammonium chloride (14.5 g , 270 mmol) in 170 mL of ethanol and 50 mL of water is heated at reflux for 1.5 hours then filtered hot through a pad of Diatomaceous earth, washing with ethanol. The filtrate is cooled to room temperature and the precipitated solids are removed by filtration. The filtrate is concentrated to a small volume and partitioned between ethyl acetate and water. The organic layer is dried over magnesium sulfate, filtered and concentrated in vacuo to provide 9.45 g of 3-fluoro-4-(2-methoxyethoxy)aniline as a brown liquid.

MS 186.13 (M+H)+ Analysis for $C_9H_{12}FNO_2$-0.2 equiv $H_2O$ Calcd: C, 57.25; H, 6.62; N, 7.46. Found: C, 57.55; H, 6.27; N, 7.50.

Reference Example 18

4-Chloro-7-fluoro-6-(2-methoxyethoxy)-3-quinolinecarbonitrile

Following the procedure of Reference Example 4, a mixture of 3-fluoro-4-(2-methoxyethoxy)aniline (6.39 g, 34.5 mmol) and ethyl (ethoxymethylene)-cyanoacetate (5.84 g, 34.5 mmol) provides 7.62 g of a brown solid. Following the procedure of Reference Example 5, this solid is converted to 6.0 g of 4-chloro-7-fluoro-6-(2-methoxyethoxy)-3-quinolinecarbonitrile, mp 130–138° C.

MS 281.02, 282.98 (M+H)+ Analysis for $C_{13}H_{10}ClFN_2O_2$-0.1 equiv $H_2O$ Calcd: C, 55.27; H, 3.64; N, 9.92. Found: C, 55.02; H, 3.64; N, 9.64.

Reference Example 19

4-({3-Chloro-4-[(1-methyl-1H-imidazol-2-yl)sulfanyl]phenyl}amino)-7-fluoro-6-(2-methoxyethoxy)-3-quinolinecarbonitrile A mixture of 4-chloro-7-fluoro-6-(2-methoxyethoxy)-3-quinolinecarbonitrile (2.72 g, 9.7 mmol), 3-chloro-4-[(1-methyl-1H-imidzaol-2-yl)thio]-benzamide (U.S. Pat. No. 4,973,599) (2.56 g, 10.6 mmol) and pyridine hydrochloride (1.2 g, 10.4 mmol) in 35 mL of 2-ethoxyethanol is heated at 110° C. for 1.5 hours then cooled to room temperature. The solids are collected by filtration, washed with diethyl ether and suspended in saturated sodium bicarbonate. After stirring for 1.5 hours, the solids are collected by filtration to provide 2.92 g of 4-({3-chloro-4-[(1-methyl-1H-imidazol-2-yl)sulfanyl]phenyl}amino)-7-fluoro-6-(2-methoxyethoxy)-3-quinolinecarbonitrile, mp 265–270° C.

MS 484.05 (M+H)+ Analysis for $C_{23}H_{19}ClFN_5O_2S$-1.7 $H_2O$ Calcd: C, 53.69; H, 4.39; N, 13.61. Found: C, 53.47; H, 4.11; N, 13.39.

Reference Example 20

4-({3-Chloro-4-[(1-methyl-1H-imidazol-2-yl)sulfanyl]phenyl}amino)-7-fluoro-6-methoxy-3-quinolinecarbonitrile Following the procedure of Reference Example 19, a mixture of 4-chloro-7-fluoro-6-methoxy-3-quinolinecarbonitrile (2.30 g , 9.72 mmol), 3-chloro-4-[(1-methyl-1H-imidazol-2-yl)thio]-benzamide (U.S. Pat. No. 4,973,599) (2.56 g, 10.6 mmol) and pyridine hydrochloride (1.2 g, 10.4 mmol) provides 3.00 g of 4-({3-chloro-4-[(1-methyl-1H-imidazol-2-yl)sulfanyl]phenyl}amino)-7-fluoro-6-methoxy-3-quinolinecarbonitrile, mp 290–294° C.

MS 440.20, 442.21, 443.22 (M+H)+ Analysis for $C_{21}H_{15}ClFN_5OS$-0.4 $H_2O$ Calcd: C, 56.41; H, 3.56; N, 15.67. Found: C, 56.63; H, 3.25; N, 15.28.

Reference Example 21

4-[(2,4-Dichloro-5-methoxyphenyl)amino]-6-ethoxy-7-fluoro-3-quinolinecarbonitrile Following the procedure of Reference Example 8, a mixture of 4-chloro-6-ethoxy-7-fluoro-3-quinolinecarbonitrile (197 mg, 0.78 mmol), 2,4-dichloro-5-methoxyaniline (220 mg, 1.14 mmol) and pyridine hydrochloride (120 mg, 1.04 mmol) provides, after flash column chromatography eluting with a gradient of dichloromethane to 1% methanol in dichloromethane, 183 mg of 4-[(2,4-dichloro-5-methoxyphenyl)amino]-6-ethoxy-7-fluoro-3-quinolinecarbonitrile, mp 184–186° C.

MS 406.0 (M+H) Analysis for $C_{19}H_{14}Cl_2FN_3O_2$-0.5 $H_2O$ Calcd: C, 54.96; H, 3.64; N, 10.12. Found: C, 54.99; H, 3.59; N, 10.05.

Reference Example 22

4-[(2,4-Dichloro-5-methoxyphenyl)amino]-7-fluoro-6-(2-methoxyethoxy)-3-quinolinecarbonitrile A mixture of 4-chloro-7-fluoro-6-(2-methoxyethoxy)-3-quinolinecarbonitrile (1.00 g, 3.59 mmol), 2,4-dichloro-5-methoxyaniline (727 mg, 3.77 mmol) and pyridine hydrochloride (620 mg, 5.34 mmol) in 18 mL of 2-ethoxyethanol is heated at 100–105° C. for 2 hours. The reaction mixture is cooled to room temperature and then poured into ice cold saturated sodium bicarbonate. The solids are collected, washed with water and then treated with methanol and dichloromethane. The mixture is filtered and the filtrate is concentrated. The solid residue is slurried with hexane, and the solids are collected by filtration to provide 1.15 g of 4-[(2,4-dichloro-5-methoxyphenyl)amino]-7-fluoro-6-(2-methoxyethoxy)-3-quinolinecarbonitrile, mp 170–172° C.

HRMS theory 436.06256; found 436.06093 (M+H)+ Analysis for $C_{20}H_{16}Cl_2FN_3O_3$-0.4 $H_2O$ Calcd: C, 54.16; H, 3.81; N, 9.48. Found: C, 53.90; H, 3.89; N, 9.36.

Reference Example 23

6-Benzyloxy-4-hydroxy-7-(2-methoxyethoxy)-3-quinolinecarbonitrile

Following the procedure used to prepare Reference Example 6, reaction of 6-benzyloxy-4-hydroxy-7-fluoro-3-quinolinecarbonitrile and 2-methoxyethanol provides 6-benzyloxy-4-hydroxy-7-(2-methoxyethoxy)-3-quinolinecarbonitrile in 86% yield, mp>250° C.

MS 351.2 (M+H)+

Reference Example 24

6-Benzyloxy-4-chloro-7-(2-methoxyethoxy)-3-quinolinecarbonitrile

Following the procedure used to prepare Reference Example 12, reaction of 6-benzyloxy-4-hydroxy-7-(2-methoxyethoxy)-3-quinolinecarbonitrile with phosphorous oxychloride provides 6-benzyloxy-4-chloro-7-(2-methoxyethoxy)-3-quinolinecarbonitrile in 67% yield, mp 142–145° C.

MS 369.1 (M+H)+ Analysis for $C_{20}H_{17}ClN_2O_3$ Calcd: C, 65.13; H, 4.65; N, 7.60. Found: C, 64.92; H, 4.90; N, 7.48.

Reference Example 25

4-Chloro-6-hydroxy-7-(2-methoxyethoxy)-3-quinolinecarbonitrile

A mixture of 6-benzyloxy-4-chloro-7-(2-methoxyethoxy)-3-quinolinecarbonitrile (512 mg, 1.39 mmol) and 0.9 mL of thioanisole in 7.5 mL of trifluoroacetic acid is heated at reflux for 3 hours then concentrated in vacuo. The residue is treated with ice water and then basified to pH 9–10 by the addition of aqueous ammonium hydroxide. The resultant suspension is extracted with ethyl acetate. The organic layer is washed with brine, dried over sodium sulfate, filtered and concentrated in vacuo. Trituration with diethyl ether provides 302 mg of 4-chloro-6-hydroxy-7-(2-methoxyethoxy)-3-quinolinecarbonitrile, mp 174–175° C.

MS 279.0 (M+H)+ Analysis for $C_{13}H_{11}ClN_2O_3$-0.8 $H_2O$ Calcd: C, 53.27; H, 4.33; N, 9.56. Found: C, 53.39; H, 4.36; N, 9.71.

Reference Example 26

6-Butoxy-4-chloro-7-(2-methoxyethoxy)-3-quinolinecarbonitrile

Following the procedure used to prepare Reference Example 14, reaction of 4-chloro-6-hydroxy-7-(2-methoxyethoxy)- 3-quinolinecarbonitrile with triphenyl phosphine, diethyl azodicarboxylate and n-butanol provides 6-butoxy-4-chloro-7-(2-methoxyethoxy)-3-quinolinecarbonitrile in 71% yield, mp 128–130° C.

MS 335.1 (M+H)+ Analysis for $C_{17}H_{19}ClN_2O_3$ Calcd: C, 60.99; H, 5.72; N, 8.37. Found: C, 61.05; H, 5.82; N, 8.10.

Reference Example 27

4-Chloro-7-fluoro-6-(2-morpholin-4-ylethoxy)-3-quinolinecarbonitrile

Following the procedure used to prepare Reference Example 14, reaction of 4-chloro-7-fluoro-6-hydroxy-3-quinolinecarbonitrile with triphenyl phosphine, diethyl azodicarboxylate and 4-(2-hydroxyethyl)morpholine provides 4-chloro-7-fluoro-6-(2-morpholin-4-ylethoxy)-3-quinolinecarbonitrile in 57% yield. An analytical sample is obtained by preparative thin layer chromatography eluting with 1% methanol in ethyl acetate, mp 163–164° C.

MS 336.1 (M+H)+ Analysis for $C_{16}H_{15}ClFN_3O_2$-0.13 Ethyl acetate Calcd: C, 57.15; H, 4.66; N, 12.10. Found: C, 57.03; H, 4.60; N, 11.96.

Reference Example 28

4-[(2,4-Dichloro-5-methoxyphenyl)amino]-7-fluoro-6-(2-morpholin-4-ylethoxy)-3-quinolinecarbonitrile Following the procedure of Reference Example 8, a mixture of 4-chloro-7-fluoro-6-(2-morpholin-4-ylethoxy)-3-quinolinecarbonitrile (136 mg, 0.41 mmol), 2,4-dichloro-5-methoxyaniline (90.5 mg, 0.47 mmol) and pyridine hydrochloride (95 mg, 0.82 mmol) provides, after preparative thin layer chromatography eluting with 7% methanol in dichloromethane, 58 mg of 4-[(2,4-dichloro-5-methoxyphenyl)amino]-7-fluoro-6-(2-morpholin-4-ylethoxy)-3-quinolinecarbonitrile, mp 166–168° C.

MS 488.9 (M–H)– Analysis for $C_{23}H_{21}Cl_2FN_4O_3$ Calcd: C, 56.22; H, 4.31; N, 11.40. Found: C, 55.91; H, 4.44; N, 11.10.

Reference Example 29

6-Methoxy-7-(4-methyl-piperazin-1-yl)-4-oxo-1,4-dihydroquinoline-3-carbonitrile

A mixture of 200 mg (0.92 mmol) of 7-fluoro-6-methoxy-4-oxo-1,4-dihydroquinoline-3-carbonitrile (Reference Example 24) and 551 mg (5.50 mmol) of N-methylpiperazine in 1 mL of 1-methyl-2-pyrrolidinone is heated at 90° C. for 8 hours, then at 105° C. for a further 16 hours. The solvents are removed in vacuo. To the resulting oily residue was added 2 mL of water and 5 mL of methanol. The solvents are again removed in vacuo. The crude product is purified by silica gel chromatography utilizing a gradient of methylene chloride/methanol (9:1 to 4:1) to yield 152 mg of 6-methoxy-7-(4-methyl-piperazin-1-yl)-4-oxo-1,4-dihydroquinoline-3-carbonitrile as a yellow solid, dec.>235° C.

$^1$HNMR (DMSO-$d_6$): δ 2.33 (s, 3H), 3.13 (broad s, 4H), 3.32 (broad s, 4H), 3.89 (s, 3H), 6.98 (s, 1H), 7.43 (s, 1H), 8.55 (s, 1H), 12.43 (broad s, 1H). MS (ES, negative ion mode): m/z calcd for $C_{16}H_{18}N_4O_2$: 298.1, found: 297.2 (M–H)–.

Reference Example 30

Ethyl 2-{[(1E)-(dimethylamino)methylidene [amino}-4-fluorobenzoate

A suspension of 2-amino-4-fluorobenzoic acid (10.2 g, 65.8 mmol) and dimethylformamide diethylacetal (58 mL) is heated at reflux for 6 h. The solution is cooled to room temperature and concentrated in vacuo. The dark oil is passed through a pad of hydrous magnesium silicate eluting with methylene chloride to provide 17.16 g of ethyl 2-{[(1 E)-(dimethylamino)methylidene]amino}-4-fluorobenzoate as a red oil.

MS 239.1 (M+H)+ Analysis for $C_{12}H_{15}FN_2O_2$-0.20 $H_2O$ Calcd: C, 59.59; H, 6.42; N, 11.58. Found: C, 59.84; H, 6.25; N, 11.29.

Reference Example 31

7-Fluoro-4-hydroxyquinoline-3-carbonitrile

To a solution of 2.5 M n-butyl lithium in tetrahydrofuran (53.6 mL, 134 mmol) in 54 mL of tetrahydrofuran at –78° C. is added dropwise a solution of acetonitrile (7.1 mL, 136 mmol) in 100 mL of tetrahydrofuran. After stirring at –78° C. for 10 min, a solution of ethyl 2-{[(1E)-(dimethylamino) methylidene]amino}-4-fluorobenzoate (14.5 g, 60.9 mmol) in 100 mL of tetrahydrofuran is added over a period of 1.5 h. After stirring at –78° C. for 2 h, the reaction temperature is slowly allowed to warm to –10° C. The mixture is then cooled to –78° C. and acetic acid (18.3 g, 305 mmol) is added dropwise. The reaction mixture is allowed to warm to room temperature and stirred for 3 days. The precipitate is collected by filtration washing with tetrahydrofuran, water, diethyl ether, ethyl acetate and then additional diethyl ether to give 7.95 g of 7-fluoro-4-hydroxyquinoline-3-carbonitrile as an off-white solid, mp>250° C.

MS 187.0 (M–H)– Analysis for $Cl_{10}H_5FN_2O$-0.20 $H_2O$ Calcd: C, 62.63; H, 2.84; N, 14.61. Found: C, 62.55; H, 2.71; N, 14.29.

Reference Example 32

4-Chloro-7-fluoroquinoline-3-carbonitrile

A mixture of 7-fluoro-4-hydroxyquinoline-3-carbonitrile (2.02 g, 10.7 mmol) and a few drops of N, N-dimethylformamide in 16.0 mL of thionyl chloride is heated at reflux for 1.5 h. The reaction mixture was concentrated in vacuo and toluene (20 mL) is added and the mixture is again concentrated in vacuo to provide 2.18 g of 4-chloro-7-fluoroquinoline-3-carbonitrile as a yellow solid, mp 163–165° C.

MS 207.0 (M+H)+

Reference Example 33

4-[(2,4-Dichloro-5-methoxyphenyl)amino]-7-fluoro-3-quinolinecarbonitrile

Following the procedure of Reference Example 8, a mixture of 4-chloro-7-fluoro-3-quinolinecarbonitrile (2.10 g, 10.2 mmol), 2,4-dichloro-5-methoxyaniline (2.15 g, 11.2 mmol) and pyridine hydrochloride (1.18 g, 10.2 mmol) provides 1.78 g of 4-[(2,4-dichloro-5-methoxyphenyl) amino]-7-fluoro-3-quinolinecarbonitrile, mp 199–201° C.

MS 360.0 (M–H)– Analysis for $C_{17}H_{10}Cl_2FN_3O$-0.4 $H_2O$ Calcd: C, 55.28; H, 2.95; N, 11.38. Found: C, 55.45; H, 2.98; N, 11.13.

Reference Example 34

7-(2-Methoxyethoxy)-4-oxo-1,4-dihydroquinoline-3-carbonitrile

A mixture of sodium hydride (500 mg, 12.5 mmol) and 7-fluoro-4-hydroxyquinoline-3-carbonitrile (1.30 g, 6.9 mmol) in 2-methoxyethanol (30 mL) is heated at reflux overnight. Additional sodium hydride (250 mg, 6.25 mmol) is added and the reaction mixture is heated at reflux overnight. Additional sodium hydride (250 mg, 6.25 mmol) is added and the reaction mixture is heated at reflux for 8 hours. The reaction mixture is cooled to room temperature and partitioned between ethyl acetate and saturated sodium bicarbonate. The basic layer is acidified with aqueous HCl and the resultant solid is collected by filtration to provide 1.05 g of 7-(2-methoxyethoxy)-4-oxo-1,4-dihydroquinoline-3-carbonitrile as a white solid, mp>250° C.

MS 243.1 (M–H)– Analysis for $C_{13}H_{12}N_2O_3 \cdot 0.25H_2O$ Calcd: C, 62.77; H, 5.07; N, 11.26. Found: C, 62.53; H, 4.68; N, 11.22.

Reference Example 35

4-Chloro-7-(2-methoxyethoxy)quinoline-3-carbonitrile

Following the procedure of Reference Example 32, 7-(2-methoxyethoxy)-4-oxo-1,4-dihydroquinoline-3-carbonitrile (800 mg, 3.28 mmol), thionyl chloride and a catalytic amount of N,N-dimethylformamide provides 748 mg of 4-chloro-7-(2-methoxyethoxy)quinoline-3-carbonitrile as an off-white solid solid, mp 143–145° C.

MS 263.2 (M+H)+

Reference Example 36

4-Chloro-6-methoxy-7-(4-methylpiperazin-1-yl)-quinoline-3-carbonitrile

A reaction mixture of 0.3 g (1.01 mmol) of 6-methoxy-7-(4-methyl-piperazin-1-yl)-4-oxo-1,4-dihydroquinoline-3-carbonitrile in 5 mL of phosphorus oxychloride is heated at 105° C. for 45 minutes. After cooling, the mixture is concentrated to dryness in vacuo to give a brown solid. To this is added 5 mL toluene, and the solution is concentrated to dryness again. Dropwise, an ice-cooled saturated aqueous sodium carbonate solution is added to the residue. This mixture is extracted with 5×25 mL of a 95:5 mixture of methylene chloride/methanol. The organic layer is dried over magnesium sulfate. The magnesium sulfate is removed by filtration, and solvent is removed in vacuo to provide 0.255 g of 4-chloro-6-methoxy-7-(4-methylpiperazin-1-yl)-quinoline-3-carbonitrile as a yellow solid, mp 177–179° C.

MS (ES, positive ion mode): m/z calcd for $C_{16}H_{17}ClN_4O$: 316.1, found: 317.0 (M+H)+. Analysis for $C_{16}H_{17}ClN_4O \cdot 0.1 H_2O$ Calcd: C, 60.32; H, 5.36; N, 17.59. Found: C, 60.00; H, 5.35; N, 17.82.

The following Reference Examples 37–41 are obtained analogously by the method of Reference Example 8 and the corresponding substituted aniline.

Reference Example 37

4-[(2,4-Dichorophenyl)amino]-7-fluoro-6-methoxyquinoline-3-carbonitrile

MP 226–229° C.; Mass Spec. 362.0 (ES+)

Reference Example 38

4-{(2,4-Dimethyl-5-methoxyphenyl)amino]-7-fluoro-6-methoxyquinoline-3-carbonitrile MP 152–153° C.; Mass Spec. 350.0 (ES+)

Reference Example 39

4-[(2-Chloro-5-methoxyphenyl)amino]-7-fluoro-6-methoxyquinoline-3-carbonitrile

MP 237° C. dec; Mass Spec. 356.0 (ES–)

Reference Example 40

7-Fluoro-6-methoxy-4-[(5-methoxy-2-methylphenyl)amino]-quinoline-3-carbonitrile

MP 169–171° C.; Mass Spec. 338.0 (ES+)

Reference Example 41

4-[(2,4-Dimethylphenyl)amino]-7-fluoro-6-methoxyquinoline-3-carbonitrile

MP 184–185° C.; Mass Spec. 320.1 (ES–)

Reference Example 42

4-Chloro-6-methoxy-7-[(1-methylpiperidin-4-yl)methoxy]quinoline-3-carbonitrile

A mixture of 7-fluoro-6-methoxy-4-oxo-1,4-dihydro-3-quinolinecarbonitrile (1.5 g, 6.9 mmol) and (1-methylpiperidin-4-yl)-methanol (1.8 g, 13.7 mmol) (WO 200471212) and a 60% dispersion in mineral oil of sodium hydride (0.8 g, 34.4 mmol) is heated at 110° C. for 2 hours. The reaction mixture is quenched with methanol, concentrated, and azeotroped with toluene to give 2.25 g of a brown solid. A mixture of this solid and phosphorous oxychloride (15 mL, 159 mmol) is heated at reflux for 30 minutes then concentrated in vacuo. The residue is partitioned between aqueous sodium bicarbonate and methylene chloride. The organic layer is dried over sodium sulfate, filtered and concentrated on to silica gel. Purification by column chromatography eluting with a gradient of 1:9 methanol:methylene chloride to 0.05:1:5 triethylamine:methanol:methylene chloride provided 1.6 g of 4-chloro-6-methoxy-7-[(1-methylpiperidin-4-yl)methoxy]quinoline-3-carbonitrile, mp 166–168° C.

MS 346 (M+H)+ Analysis for $C_{18}H_{20}ClN_3O_{2l} \cdot 1$ HCl+0.5 $H_2O$ Calcd: C, 54.72; H, 5.54; N 10.50. Found: C, 54.72; H, 6.07; N 10.05.

EXAMPLE 1

7-(2-Butynyloxy)-4-[(2,4-dichloro-5-methoxyphenyl)amino]-6-methoxy-3-quinolinecarbonitrile A mixture of 2-butyn-1-ol (2.02 g, 28.8 mmol) and sodium (65 mg, 1.53 mmol) is heated at 120° C. for 20 minutes. 4-[2,4-Dichloro-5-methoxyphenyl)amino]-7-fluoro-6-methoxy-3-quinolinecarbonitrile (150 mg, 0.38 mmol) is added and the reaction mixture is heated at 120° C. overnight, then cooled to room temperature. The reaction mixture is added to water and acidified with acetic acid. The solids are collected by filtration and purified by flash column chromatography, eluting with a gradient of 3:7 ethyl acetate:hexane to 1:1 ethyl acetate:hexane, to provide 116 mg of 7-(2-butynyloxy)-4-[(2,4-dichloro-5-methoxyphenyl)amino]-6-methoxy-3-quinolinecarbonitrile, mp 193–197° C.

MS 442.1(M+H)+ Analysis for $C_{22}H_{17}Cl_2N_3O_3$ Calcd: C, 59.74; H, 3.87; N, 9.50. Found: C, 59.65; H, 3.75; N, 9.30.

EXAMPLE 2

4-[(2,4-Dichloro-5-methoxyphenyl)amino]-7-(3-dimethylamino-2,2-dimethylpropoxy)-6-methoxy-3-quinolinecarbonitrile A mixture of sodium (48 mg, 2.1 mmol) in 2 mL of 3-dimethylamino-2,2-dimethylpropanol is heated at 100° C.

for 20 minutes. 4-[2,4-Dichloro-5-methoxyphenyl)amino]-7-fluoro-6-methoxy-3-quinolinecarbonitrile (200 mg, 0.51 mmol) is added and the reaction mixture is heated at 100° C. for 7 hours, then cooled to room temperature. The reaction mixture is partitioned between saturated sodium bicarbonate and ethyl acetate. The organic layer is washed with water, dried over sodium sulfate, filtered and concentrated in vacuo. The residue is purified by flash column chromatography eluting with 1:1 hexane:ethyl acetate to provide 58 mg of 4-[(2,4-dichloro-5-methoxyphenyl)amino]-7-(3-dimethylamino-2,2-dimethylpropoxy)-6-methoxy-3-quinolinecarbonitrile, mp 178–180° C.

HRMS theory 503.16113; found 503.16112 (M+H)+ Analysis for $C_{25}H_{28}Cl_2N_4O_3$-1.2 $H_2O$ Calcd: C, 57.19; H, 5.84; N, 10.67. Found: C, 57.27; H, 6.19; N, 10.49.

EXAMPLE 3

4-[(2,4-Dichloro-5-methoxyphenyl)amino]-7-[3-(1,1-dioxido-4-thiomorpholinyl)propoxy]-6-methoxy-3-quinolinecarbonitrile A mixture of sodium (48 mg, 2.1 mmol) in 2 mL of 3-(1,1-dioxothiomorpholinyl)-1-propanol (WO 20047212) is heated at 100° C. for 1 hour. 4-[(2,4-Dichloro-5-methoxyphenyl)amino]-7-fluoro-6-methoxy-3-quinolinecarbonitrile (200 mg, 0.51 mmol) is added and the reaction mixture is heated at 100° C. for 4 hours, then cooled to room temperature. The reaction mixture is poured into saturated sodium bicarbonate and the solids are collected by filtration. The residue is purified by flash column chromatography eluting with 5% methanol in dichloromethane to provide 88 mg of 4-[(2,4-dichloro-5-methoxyphenyl)amino]-7-[3-(1,1-dioxido-4-thiomorpholinyl)propoxy]-6-methoxy-3-quinolinecarbonitrile, mp 118–120° C.

HRMS theory 565.10735; found 565.10674 (M+H)+ Analysis for $C_{25}H_{26}Cl_2N_4O_5S$-1.1 $H_2O$ Calcd: C, 51.30; H, 4.86; N, 9.57. Found: C, 51.11; H, 4.70; N, 9.26.

EXAMPLE 4

4-[(2,4-Dichloro-5-methoxyphenyl)amino]-6-methoxy-7-}2-[2-(1-piperazinyl)ethoxylethoxy)-3-quinolinecarbonitrile A mixture of sodium (50 mg, 2.2 mmol) in 1 mL of 2-[2-(1-piperazinyl)ethoxy]ethanol is heated at 120° C. for 2 hours. 4-[(2,4-Dichloro-5-methoxyphenyl)amino]-7-fluoro-6-methoxy-3-quinolinecarbonitrile (150 mg, 0.38 mmol) is added and the reaction mixture is heated at 140–145° C. for 2 hours, then cooled to room temperature. The reaction mixture is partitioned between saturated sodium bicarbonate and ethyl acetate. The organic layer is dried over magnesium sulfate, filtered and concentrated in vacuo. The residue is purified by flash column chromatography eluting with a gradient of 3% methanol in dichloromethane to 1% ammonium hydroxide and 30% methanol in dichloromethane followed by recrystallization from acetone and hexane to provide 124 mg of 4-[(2,4-dichloro-5-methoxyphenyl)amino]-6-methoxy-7-{2-[2-(1-piperazinyl)-ethoxy]ethoxy)-3-quinolinecarbonitrile, mp 88–90° C.

MS 273.4, 274.2 Analysis for $C_{26}H_{29}Cl_2N_5O_4$-1.5 $H_2O$-0.2 acetone Calcd: C, 54.60; H, 5.70; N, 11.97. Found: C, 54.68; H, 5.75; N, 11.76.

EXAMPLE 5

4-[(2,4-Dichloro-5-methoxyphenyl)amino]-6-methoxy-7-(2-thienylmethoxy)-3-quinolinecarbonitrile To a mixture of sodium hydride (37 mg, 1.54 mmol) in 3 mL of dimethylsulfoxide is added 2-thiophenemethanol (48 mg, 0.42 mmol). The solution is stirred at room temperature for 45 minutes. 4-[(2,4-Dichloro-5-methoxyphenyl)amino]-7-fluoro-6-methoxy-3-quinolinecarbonitrile (150 mg, 0.38 mmol) is added and the reaction mixture is heated at 100° C. overnight, then cooled to room temperature. The reaction mixture is poured into saturated sodium bicarbonate and the solids are collected by filtration. Purification by flash column chromatography eluting with 1:1 hexane:ethyl acetate provides 61 mg of 4-[(2,4-dichloro-5-methoxyphenyl)amino]-6-methoxy-7-(2-thienylmethoxy)-3-quinolinecarbonitrile, mp 194–196° C.

MS 485.9, 488.0 (M+H)+ Analysis for $C_{23}H_{17}Cl_2N_3O_3S$ Calcd: C, 56.80; H, 3.52; N, 8.64. Found: C, 56.71; H, 3.74; N, 8.46.

EXAMPLE 6

7-Benzyloxy-4-[(2,4-dichloro-5-methoxyphenyl)amino]-6-methoxy-3-quinolinecarbonitrile To a mixture of sodium hydride (122 mg, 3.04 mmol) in 6 mL of dimethylsulfoxide is added benzyl alcohol (91 mg, 0.84 mmol). The solution is stirred at room temperature for 40 minutes. 4-[(2,4-Dichloro-5-methoxyphenyl)amino]-7-fluoro-6-methoxy-3-quinolinecarbonitrile (300 mg, 0.76 mmol) is added and the reaction mixture is heated at 100° C. for 3 hours then cooled to room temperature and allowed to stir overnight. The reaction mixture is poured into saturated sodium bicarbonate and the solids are collected by filtration. Purification by flash column chromatography eluting with 10% ethyl acetate in dichloromethane provides 267 mg of 7-benzyloxy-4-[(2,4-dichloro-5-methoxyphenyl)amino]-6-methoxy-3-quinolinecarbonitrile, mp 198–200° C.

HRMS theory 480.08763; found 480.08725 (M+H)+ Analysis for $C_{25}H_{19}Cl_2N_3O_3$ Calcd: C, 62.51; H, 3.99; N, 8.75. Found: C, 62.31; H, 4.20; N, 8.70.

EXAMPLE 7

4-[(2,4-Dichloro-5-methoxyphenyl)amino]-7-ethylsulfanyl-6-methoxy-3-quinolinecarbonitrile To a mixture of sodium hydride (82 mg, 2.04 mmol) in 6 mL of tetrahydrofuran is added ethanethiol (77 mg, 1.12 mmol) in 6 mL of tetrahydrofuran. The reaction mixture is stirred at room temperature for 2 hours. A solution of 4-[(2,4-dichloro-5-methoxyphenyl)amino]-7-fluoro-6-methoxy-3-quinolinecarbonitrile (200 mg, 0.51 mmol) in 7 mL of tetrahydrofuran is added via syringe and the reaction mixture is heated at 70° C. for 5 hours, then cooled to room temperature. The reaction volume is reduced by concentration in vacuo and then partitioned between ethyl acetate and water. The aqueous layer is extracted with additional ethyl acetate and the organic layers are combined and washed with water. The organic layer is dried over magnesium sulfate, filtered and concentrated in vacuo. The residue is purified by flash column chromatography eluting with a gradient of 10% to 30% ethyl acetate in hexane to provide 154 mg of 4-[(2,4-dichloro-5-methoxyphenyl)amino]-7-ethylsulfanyl-6-methoxy-3-quinolinecarbonitrile, mp 212–214° C.

HRMS theory 434.04913; found 434.04989 (M+H)+ HRMS theory 867.09098; found 867.09317 (2M+H)+ Analysis for $C_{25}H_{19}Cl_2N_3O_3$-0.3 $H_2O$ Calcd: C, 54.62; H, 4.03; N, 9.56. Found: C, 54.32; H, 4.06; N, 9.50.

EXAMPLE 8

4-[(2,4-Dichloro-5-methoxyphenyl)amino]-6-methoxy-7-phenylsulfanyl-3-quinolinecarbonitrile A mixture of sodium thiophenoxide (181 mg, 1.37 mmol) and 4-[(2,4-dichloro-5-methoxyphenyl)amino]-7-fluoro-6- methoxy-3-quinolinecarbonitrile (100 mg, 0.27 mmol) in 3 mL of tetrahydrofuran is heated at reflux overnight. N-methylpyrrolidone (2 mL) is added and the reaction mixture is heated at 120° C. for 1 hour then at 140° C. for for 45 min. An additional 100 mg of sodium thiophenol is added and the reaction mixture is heated at 140° C. for 3 hours. The reaction mixture is partitioned between ethyl acetate and water. The organic layer is dried over sodium sulfate, filtered and concentrated in vacuo. The residue is purified by flash column chromatography eluting with a 1:4 ethyl acetate:hexane to provide 36 mg of 4-[(2,4-dichloro-5-methoxyphenyl)amino]-6-methoxy-7-phenylsulfanyl-3-quinolinecarbonitrile, mp 220–222° C.

MS 481.7, 483.7 (M+H)+ Analysis for $C_{24}H_{17}Cl_2N_3O_2S$ Calcd: C, 54.62; H, 4.03; N, 9.56. Found: C, 54.32; H, 4.06; N, 9.50.

EXAMPLE 9

4-Cyclopentylamino-6-methoxy-7-(2-methoxyethoxy)-3-quinolinecarbonitrile

A mixture of 4-cyclopentylamino-7-fluoro-6-methoxy-3-quinolinecarbonitrile (150 mg, 0.53 mmol) and sodium hydride (53 mg, 2.21 mmol) in 1.6 mL of 2-methoxyethanol is heated at reflux for 30 minutes, then cooled to room temperature. The reaction mixture is partitioned between aqueous sodium bicarbonate and ethyl acetate. The organic phase is dried over sodium sulfate, filtered and concentrated in vacuo. Purification by preparative thin layer chromatography, eluting with 5% methanol in dichloromethane, followed by trituration with methanol and diethyl ether, provides 95 mg of 4-cyclopentylamino-6-methoxy-7-(2-methoxyethoxy)-3-quinolinecarbonitrile, mp 87–90° C.

MS 342.23 (M+H)+ Analysis for $C_{19}H_{23}N_3O_3 \cdot 0.20\ H_2O$ Calcd: C, 65.12; H, 6.90; N, 11.99. Found: C, 64.88; H, 6.88; N, 12.13.

EXAMPLE 10

4-Butylamino-6-methoxy-7-(2-methoxyethoxy)-3-quinolinecarbonitrile

A mixture of 4-butylamino-7-fluoro-6-methoxy-3-quinolinecarbonitrile (150 mg, 0.55 mmol) and sodium hydride (55 mg, 2.29 mmol) in 1.7 mL of 2-methoxyethanol is heated at reflux for 30 minutes then cooled to room temperature. The reaction mixture is partitioned between aqueous sodium bicarbonate and ethyl acetate. The organic phase is dried over sodium sulfate, filtered and concentrated in vacuo. Purification by preparative thin layer chromatography, eluting with 5% methanol in dichloromethane, followed by trituration with ethyl acetate, provides 135 mg of 4-butylamino-6-methoxy-7-(2-methoxyethoxy)-3-quinolinecarbonitrile, mp 99–102° C.

MS 330.24 (M+H)+ $^1$H NMR (DMSO-$d_6$) δ 0.94 (t, 3H), 1.42 (m, 2H), 1.70 (m, 2H), 3.32 (s, 3H), 3.33 (s, 3H), 3.70–3.78 (m, 4H), 4.23 (m, 2H), 7.23 (s, 1H), 7.62 (s, 1H), 7.85 (t, 1H), 8.31 (s, 1H).

EXAMPLE 11

7-Benzylthio-4-[(2,4-dichloro-5-methoxyphenyl)amino]-6-methoxy-3-quinolinecarbonitrile A mixture of sodium hydride (169 mg, 4.2 mmol), benzyl mercaptan (145 mg, 1.2 mmol) and 4-[(2,4-dichloro-5-methoxyphenyl)amino]-7-fluoro-6-methoxy-3-quinolinecarbonitrile (250 mg, 0.64 mmol) in 1 mL of tetrahydrofuran is heated at 70° C. for 1 hour, then stirred at room temperature overnight. Upon addition of 1 mL of dimethyl sulfoxide a solution is obtained. Additional amounts of sodium hydride and benzyl mercaptan are added and the reaction mixture is heated at 100° C. The reaction mixture is partitioned between ethyl acetate and water. The organic layer is dried over sodium sulfate, filtered and concentrated in vacuo. The residue is purified by preparative thin layer chromatography, eluting with 1:2 ethyl acetate:hexane to provide 150 mg of 7-benzylthio-4-[(2,4-dichloro-5-methoxyphenyl)amino]-6-methoxy-3-quinolinecarbonitrile, mp 123–125° C.

MS 494.03 (M−H)− Analysis for $C_{25}H_{19}Cl_2N_3O_2S \cdot 0.5\ H_2O$ Calcd: C, 59.40; H, 3.99; N, 8.31. Found: C, 59.45; H, 3.98; N, 8.12.

EXAMPLE 12

4-[(2,4-Dichloro-5-methoxyphenyl)amino]-6-methoxy-7-(pyridin-4-yloxy)-3-quinolinecarbonitrile A mixture of sodium hydride (128 mg, 3.2 mmol) and 4-hydroxypyridine (750 mg, 7.89 mmol) in 5 mL of N,N'-dimethylformamide is heated at 100° C. for 1 hour. 4-[(2,4-Dichloro-5-methoxyphenyl)amino]-7-fluoro-6-methoxy-3-quinolinecarbonitrile (200 mg, 0.51 mmol) is added and the reaction mixture is heated at 130° C. for 2 hours. An additional 21 mg of sodium hydride is added and the reaction mixture is heated at 130° C. for an additional 30 minutes. The reaction mixture is partitioned between ethyl acetate and water. The organic layer is dried over sodium sulfate, filtered and concentrated in vacuo. The residue is purified by heating with methanol and dichloromethane to provide 130 mg of 4-[(2,4-dichloro-5-methoxyphenyl)amino]-6-methoxy-7-(pyridin-4-yloxy)-3-quinolinecarbonitrile, mp 267–269° C.

MS 467.11 (M+H)+ Analysis for $C_{23}H_{16}Cl_2N_4O_3 \cdot 0.2$ ethyl acetate Calcd: C, 58.89; H, 3.33; N, 11.55. Found: C, 58.84; H, 3.41; N, 11.60.

EXAMPLE 13

4-[(2,4-Dichloro-5-methoxyphenyl)amino]-6-methoxy-7-[2-(1-methylpiperidin-4-yl)ethoxy]-3-quinolinecarbonitrile A mixture of sodium hydride (128 mg, 3.2 mmol) and 1-methyl-4-piperidineethanol (180 mg, 1.25 mmol) [EP 0581538] in 5 mL of N, N'-dimethylformamide is heated at 110° C. for 1 hour. 4-[(2,4-Dichloro-5-methoxyphenyl)amino]-7-fluoro-6-methoxy-3-quinolinecarbonitrile (200 mg, 0.51 mmol) is added and the reaction mixture is heated at 135° C. for 5 hours. Over the next 4 hours an additional 128 mg of sodium hydride is added to the reaction mixture at 130° C. The reaction mixture is partitioned between ethyl acetate and water. The organic layer is dried over sodium sulfate, filtered and concentrated in vacuo. The residue is purified by preparative thin layer chromatography, eluting with 20% methanol in dichloromethane to provide 105 mg of 4-[(2,4-dichloro-5-methoxyphenyl)amino]-6-methoxy-7-[(2-(1-methylpiperidin-4-yl)ethoxy]-3-quinolinecarbonitrile, mp 190–191° C.

MS 515.19 (M+H)+ Analysis for $C_{26}H_{28}Cl_2N_4O_3 \cdot 1.0\ H_2O$ Calcd: C, 58.53; H, 5.67; N, 10.50. Found: C, 58.65; H, 5.57; N, 10.34.

EXAMPLE 14

4-[(2,4-Dichloro-5-methoxyphenyl)amino]-6-methoxy-7-[2-methoxyethoxy]-3-quinolinecarbonitrile A mixture of sodium (118 mg, 5.11 mmol) and 2-methoxyethanol (5 mL) is heated at 120–130° C. for 3 hours. 4-[(2,4-Dichloro-5-methoxyphenyl)amino]-7-fluoro-6-methoxy-3-quinolinecarbonitrile (500 mg, 1.28 mmol) is added and the reaction mixture is heated at 120–125° C. for 1 hour. The temperature of the reaction mixture is increased to 140–150° C. and this temperature is maintained for 2.5 hours. The reaction mixture is cooled to room temperature and diluted with ice cold aqueous sodium bicarbonate. The solid is collected by filtration washing with water and hexane. Purification by flash column chromatography, eluting with 2% methanol in dichloromethane provides 550 mg of 4-[(2,4-dichloro-5-methoxyphenyl)amino]-6-methoxy-7-[2-methoxyethoxy]-3-quinolinecarbonitrile, mp 210–212° C.

MS 448.2(M+H)+ Analysis for $C_{21}H_{19}Cl_2N_3O_4$ Calcd: C, 56.26; H, 4.27; N, 9.37. Found: C, 56.02; H,4.16; N, 9.12.

EXAMPLE 15

4-[(2,4-Dichloro-5-methoxyphenyl)amino]-6-methoxy-7-[2-(1-methyl-3-piperidinyl)methoxy]-3-quinolinecarbonitrile To a solution of 4-[(2,4-dichloro-5-methoxyphenyl)amino]-7-fluoro-6-methoxy-3-quinolinecarbonitrile (250 mg, 0.64 mmol) and 1-methylpiperidine-3-methanol (165 mg, 1.28 mmol) in 6 mL of N, N'-dimethylformamide at 135° C. is added sodium hydride (92 mg, 3.8 mmol) in portions. After 1 hour an additional 92 mg of sodium hydride is added to the reaction mixture at 135° C. After 30 minutes the reaction mixture is poured into saturated sodium bicarbonate. After stirring for 15 minutes the solid is collected by filtration. The residue is purified by flash column chromatography, eluting with a gradient of 5% methanol in dichloromethane to 1% ammonium hydroxide in 10% methanol in dichloromethane. After an additional purification by flash column chromatography eluting with a gradient of 5% methanol in dichloromethane to 25% methanol in dichloromethane, 4-[(2,4-dichloro-5-methoxyphenyl)amino]-6-methoxy-7-[(2-(1-methyl-3-piperidinyl)methoxy]-3-quinolinecarbonitrile is obtained, mp 176–178° C.

MS 499.09 (M–H)– Analysis for $C_{25}H_{26}Cl_2N_4O_3$-0.3 $H_2O$ Calcd: C, 59.25; H, 5.29; N, 11.06. Found: C, 59.18; H, 5.20; N, 10.91.

EXAMPLE 16

4-[(2,4-Dichloro-5-methoxyphenyl)amino]-6-methoxy-7-[2-(1-methyl-4-piperidinyl)methoxy]-3-quinolinecarbonitrile To a solution of 4-[(2,4-dichloro-5-methoxyphenyl)amino]-7-fluoro-6-methoxy-3-quinolinecarbonitrile (600 mg, 1.53 mmol) and 1-methylpiperidine-4-methanol (395 mg, 3.06 mmol) (WO 20047212) in 10 mL of N, N'-dimethylformamide at 135° C. is added sodium hydride (362 mg, 9.06 mmol) in portions. After 45 minutes the reaction mixture is poured into saturated sodium bicarbonate. After stirring for 15 minutes the solid is collected by filtration. The residue is purified by flash column chromatography, eluting with a gradient of 5% methanol in dichloromethane to 25% methanol in dichloromethane. Trituation with diethyl ether provides 396 mg of 4-[(2,4-dichloro-5-methoxyphenyl)amino]-6-methoxy-7-[(2-(1-methyl-4-piperidinyl)methoxy]-3-quinolinecarbonitrile, mp 200–202° C.

MS 501.3 (M+H)+ Analysis for $C_{25}H_{26}Cl_2N_4O_3$-0.8$H_2O$ Calcd: C, 58.21; H, 5.39; N, 10.86. Found: C, 58.19; H, 5.23; N, 10.67.

EXAMPLE 17

6-Methoxy-7-[2-methoxyethoxy]-4-[(3,4,5-trimethoxyphenyl)amino]-3-quinolinecarbonitrile A mixture of sodium hydride (80 mg, 2.0 mmol) and 6-methoxy-7-fluoro-4-[(3,4,5-tri-methoxyphenyl)amino]-3-quinolinecarbonitrile (203 mg, 0.53 mmol) in 2-methoxyethanol (6 mL) is heated at reflux for 2 hours. Additional sodium hydride (80 mg, 2.0 mmol) is added and the reaction mixture is heated at reflux for 4 hours. The reaction mixture is cooled to room temperature and partitioned between ethyl acetate and saturated sodium bicarbonate. The organic layer is dried over magnesium sulfate, filtered and concentrated in vacuo. Trituration of the residue with ethyl acetate and diethyl ether provides 178 mg of 6-methoxy-7-[2-methoxyethoxy]-4-[(3,4,5-trimethoxyphenyl)amino]-3-quinolinecarbonitrile, mp 188–190° C.

MS 440.22 (M+H)+ Analysis for $C_{23}H_{25}N_3O_{6-1.0}$ $H_2O$ Calcd: C, 60.38; H, 5.95; N, 9.19. Found: C, 60.44; H, 5.98; N, 9.15.

EXAMPLE 18

6-Methoxy-7-[(1-methylpiperidine-4-yl)methoxyl-4-[(3,4,5-trimethoxyphenyl)amino]-3-quinolinecarbonitrile Following the procedure used to prepare Example 15, 6-methoxy-7-fluoro-4-[(3,4,5-tri-methoxyphenyl)amino]-3-quinolinecarbonitrile (230 mg, 0.60 mmol) and 1-methylpiperidine-3-methanol (200 mg, 1.55 mmol) provides, after flash column chromatography eluting with a gradient of 3:1 ethyl acetate:methanol to 2% aqueous ammonium hydroxide in 3:1 ethyl acetate:methanol, 143 mg of 6-methoxy-7-[(1-methylpiperidine-4-yl)methoxy]]-4-[(3,4,5-trimethoxyphenyl)amino]-3-quinolinecarbonitrile, mp softens at 65° C.

MS 493.26 (M+H)+ Analysis for $C_{27}H_{32}N_4O_5$-2.5 $H_2O$ Calcd: C, 60.32; H, 6.94; N, 10.42. Found: C, 60.28; H, 6.71; N, 10.35.

EXAMPLE 19

4-({3-Chloro-4-[(1-methyl-1H-imidazol-2-yl)sulfanyl]phenyl}amino)-6-methoxy-7-[2-(2-methoxy)ethoxy]-3-quinolinecarbonitrile A mixture of sodium (78 mg, 3.4 mmol) in 2 mL of 2-(2-methoxyethoxy)ethanol is heated at 100° C. for 1 hour. 4-({3-Chloro-4-[(1-methyl-1H-imidazol-2-yl)sulfanyl]phenyl}amino)-7-fluoro-6-methoxy-3-quinolinecarbonitrile (300 mg, 0.68 mmol) is added and the reaction mixture is heated at 140° C. for 3.5 hours, then cooled to room temperature. The reaction mixture is poured into saturated sodium bicarbonate and the solids are collected by filtration, washing with water. Purification by flash column chromatography eluting with a gradient of 2% methanol in dichloromethane to 3% methanol in dichloromethane followed by recrystallization from acetone and hexane provides 262 mg of 4-({3-chloro-4-[(1-methyl-1H-imidazol-2-yl)sulfanyl]phenyl}amino)-6-methoxy-7-[2-(2-methoxy)ethoxy]-3-quinolinecarbonitrile, mp 222–224° C.

MS 540.35, 542.39 (M+H)+ Analysis for $C_{26}H_{26}ClN_5O_4S$-0.5 $H_2O$ Calcd: C, 56.87; H, 4.96; N, 12.76. Found: C, 56.75; H, 4.78; N, 12.72.

EXAMPLE 20

4-({3-Chloro-4-[(1-methyl-1H-imidazol-2-yl)sulfanyl]phenyl}amino)-7-[3-(dimethylamino)propoxy)-6-(2-methoxyethoxy)-3-quinolinecarbonitrile Following the procedure of Example 19, 4-({3-chloro-4-[(1-methyl-1H-imidazol-2-yl)sulfanyl]phenyl}amino)-7- fluoro-6-(2-methoxyethoxy)-3-quinolinecarbonitrile (300 mg, 0.62 mmol) and 2 mL of 3-dimethylamino-1-propanol provides 115 mg of 4-({3-chloro-4-[(1-methyl-1H-imidazol-2-yl)sulfanyl]phenyl}amino)-7-[3-(dimethylamino)propoxy]-6-(2-methoxyethoxy)-3-quinolinecarbonitrile, mp 194–203° C.

MS 567.31 (M+H)+, 284.16 (M+2H)2+ Analysis for $C_{28}H_{31}ClN_6O_3S$-1.4 $H_2O$ Calcd: C, 56.77; H, 5.75; N, 14.19. Found: C, 56.61; H, 5.35; N, 13.90.

EXAMPLE 21

4-({3-Chloro-4-[(1-methyl-1H-imidazol-2-yl)sulfanyl]phenyl}amino)-7-[3-(4-ethyl-1-piperazinyl)propoxy]-6-(2-methoxyethoxy)-3-quinolinecarbonitrile Following the procedure of Example 15, 4-({3-chloro-4-[(1-methyl-1H-imidazol-2-yl)sulfanyl]phenyl}amino)-7-fluoro-6-(2-methoxyethoxy)-3-quinolinecarbonitrile (300 mg, 0.62 mmol) and 1-ethyl-4-(3-hydroxypropyl)piperazine (540 mg, 3.1 mmol) provides 155 mg of 4-({3-chloro-4-[(1-methyl-1H-imidazol-2-yl)sulfanyl]phenyl}amino)-7-[3-(4-ethyl-1-piperazinyl)propoxy]-6-(2-methoxyethoxy)-3-quinolinecarbonitrile, mp 188–190° C.

MS 318.68 (M+2H)+2 Analysis for $C_{32}H_{38}ClN_7O_3S$ -1.0 $H_2O$ Calcd: C, 58.74; H, 6.16; N, 14.99. Found: C, 58.84; H, 5.91; N, 14.73.

EXAMPLE 22

4-[(2,4-Dichloro-5-methoxyphenyl)amino]-6-[2-methoxyethoxy]-7-[(1-methylpiperidine-4-yl)methoxy]3-quinolinecarbonitrile Following the procedure used to prepare Example 15, 4-[(2,4-dichloro-5-methoxyphenyl)amino]-7-fluoro-6-[2-methoxyethoxy]-3-quinolinecarbonitrile (300 mg, 0.69 mmol) and 1-methylpiperidine-4-methanol (178 mg, 1.38 mmol) provides, after preparatory thin layer chromatography eluting with 20% methanol in ethyl acetate, 165 mg of 4-[(2,4-dichloro-5-methoxyphenyl)amino]-6-[2-methoxyethoxy]-7-[(1-methylpiperidine-4-yl)methoxy]-3-quinolinecarbonitrile, mp 153–155° C.

MS 545.19 (M+H)+ Analysis for $C_{27}H_{30}Cl_2N_4O_4$-0.7 $H_2O$ Calcd: C, 58.11; H, 5.67; N, 10.04. Found: C, 58.04; H, 5.74; N, 9.99.

EXAMPLE 23

4-[(2,4-Dichloro-5-methoxyphenyl)amino]-6-ethoxy-7-(2-methoxyethoxy)3-quinolinecarbonitrile Following the procedure used to prepare Example 17, 4-[(2,4-dichloro-5-methoxyphenyl)amino]-6-ethoxy-7-fluoro-3-quinolinecarbonitrile (138 mg, 0.34 mmol) and 2-methoxyethanol provides 105 mg of 4-[(2,4-dichloro-5-methoxyphenyl)amino]-6-ethoxy-7-(2-methoxyethoxy)3-quinolinecarbonitrile, mp 215–217° C.

MS 462.1 (M+H)+ Analysis for $C_{22}H_{31}Cl_2N_3O_4$-0.3 $H_2O$ Calcd: C, 56.49; H, 4.66; N, 8.99. Found: C, 56.59; H, 4.64; N, 8.95.

EXAMPLE 24

6-Butoxy-4-[(2,4-dichloro-5-methoxyphenyl)amino]-7-(2-methoxyethoxy)-3-quinolinecarbonitrile A mixture of 6-butoxy-4-chloro-7-(2-methoxyethoxy)-3-quinolinecarbonitrile (184 mg, 0.55 mmol), 2,4-dichloro-5-methoxyaniline (127 mg, 0.66 mmol) and pyridine hydrochloride (76 mg, 0.66 mmol) in 5 mL of 2-ethoxyethanol is heated at 120° C. for 7 hours. The reaction mixture is cooled to room temperature and concentrated in vacuo. Diethyl ether is added to the residue and the solids are collected and suspended in saturated aqueous sodium bicarbonate. After stirring for 1 hour the solids are collected by filtration and washed with water. Purification by preparatory thin layer chromatography, eluting with 7% methanol in dichloromethane provides 93 mg of 6-butoxy-4-[(2,4-dichloro-5-methoxyphenyl)amino]-7-(2-methoxyethoxy)-3-quinolinecarbonitrile, mp 166–167° C.

MS 488.0 (M–H)– Analysis for $C_{24}H_{25}Cl_2N_3O_4$-0.5 $H_2O$ Calcd: C, 57.72; H, 5.25; N, 8.41. Found: C, 57.67; H, 4.93; N, 8.49.

EXAMPLE 25

4-[(2,4-Dichloro-5-methoxyphenyl)amino]-6-methoxy-7-(tetrahydro-2H-pyran-2-ylmethoxy)3-quinolinecarbonitrile Following the procedure used to prepare Example 15, 4-[(2,4-dichloro-5-methoxyphenyl)amino]-6-ethoxy-7-fluoro-3-quinolinecarbonitrile (250 mg, 0.64 mmol) and tetrahydropyran-2-methanol provides 177 mg of 4-[(2,4-dichloro-5-methoxyphenyl)amino]-6-methoxy-7-(tetrahydro-2H-pyran-2-ylmethoxy)-3-quinolinecarbonitrile, mp 193–196° C.

MS 485.9 (M–H)– Analysis for $C_{24}H_{23}Cl_2N_3O_4$ Calcd: C, 59.03; H, 4.75; N, 8.60. Found: C, 59.06; H, 4.84; N, 8.39.

EXAMPLE 26

4-[(2,4-Dichloro-5-methoxyphenyl)amino]-7-(2-methoxyethoxy)-6-(2-morpholin-4-ylethoxy)3-quinolinecarbonitrile Following the procedure used to prepare Example 15, 4-[(2,4-dichloro-5-methoxyphenyl)amino]-7-fluoro-6-(2-morpholin-4-ylethoxy)-3-quinolinecarbonitrile (102 mg, 0.21 mmol) and 2-methoxyethanol provides 86 mg of 4-[(2,4-dichloro-5-methoxyphenyl)amino]-7-(2-methoxyethoxy)-6-(2-morpholin-4-ylethoxy)3-quinolinecarbonitrile, mp 158–159° C.

MS 544.9 (M–H)– Analysis for $C_{26}H_{28}Cl_2N_4O_5$-1.3 $H_2O$ Calcd: C, 54.70; H, 5.40; N, 9.81. Found: C, 54.57; H, 5.24; N, 9.79.

EXAMPLE 27

4-[3-Chloro-4-(1-methyl-1H-imidazol-2-ylsulfanyl)-phenylamino]-6-methoxy-7-(4-methylpiperazin-1-yl)-quinoline-3-carbonitrile A mixture of 200 mg (0.455 mmol) of 4-[3-chloro-4-(1-methyl-1H-imidazol-2-ylsulfanyl)-phenylamino]-7-fluoro-6-methoxyquinoline-3-carbonitrile (Reference Example 20) and 273 mg (2.73 mmol) of N-methylpiperazine in 1 mL of 1-methyl-2-pyrrolidinone was heated at 105° C. for 16 hours. The solvents are removed in vacuo. A 10 mL portion of water is added to the residue, from which a tan solid precipitates out. The solid is filtered off and washed with water. After drying in vacuo, the solid is suspended in ethyl acetate and stirred for 1 hour. The solid is filtered off, washed with ethyl acetate and dried in vacuo to provide 0.175 g of 4-[3-chloro-4-(1-methyl-1H-imidazol-2-ylsulfanyl)-phenylamino]-6-methoxy-7-(4-methypiperazin-1-yl)-quinoline-3-carbonitrile as a yellow solid, mp 270–272° C.

¹HNMR (DMSO-d₆): δ 2.24(s, 3H), 3.19 (broad s, 4H), 3.32 (broad s, 4H), 3.60 (s, 3H), 3.92 (s, 3H), 6.58 (d, J=6.3 Hz, 1H), 7.10 (dd, J=1.5 Hz, J=6.6 Hz, 1,H), 7.15 (d, J=0.9 Hz, 1H), 7.24 (s, 1H), 7.37 (d, J=1.8 Hz), 7.53 (d, J=0.6 Hz), 7.60 (s, 1H), 8.48 (s, 1H), 9.52 (s, 1H).

MS (ES, negative ion mode): m/z calcd for $C_{26}H_{26}ClN_7OS$: 519.2, found: 518.3 (M-H)⁻ Analysis for $C_{26}H_{26}ClN_7OS \cdot 1.0\ H_2O$ Calcd: C, 58.04; H, 5.25; N, 18.22. Found: C, 58.16; H, 4.94; N, 17.95.

EXAMPLE 28

4-[(2,4-Dichloro-5-methoxyphenyl)amino]-6-methoxy-7-{[3-(1-methylpiperidin-4-yl)propyl]amino}quinoline-3-carbonitrile Following the procedure used to prepare Example 27, 250 mg (0.64 mmol) of 4-[(2,4-dichloro-5-methoxyphenyl)amino]-7-fluoro-6-methoxyquinoline-3-carbonitrile is reacted with 600 mg (3.80 mmol) of 3-(1-methylpiperidin-4-yl)propylamine in 2 mL of 1-methyl-2-pyrrolidinone at 105° C. for 18 hours to yield 130 mg of 4-[(2,4-dichloro-5-methoxyphenyl)amino]-6-methoxy-7-{[3-(1-methylpiperidin-4-yl)propyl]amino}quinoline-3-carbonitrile as a white solid, mp 122–124° C.

MS (ES, positive ion mode): m/z calcd for $C_{27}H_{31}Cl_2N_5O$: 573.2, found: 528.2 (M+H)⁺. Analysis for $C_{27}H_{31}Cl_2N_5O$ Calcd: C, 61.36; H, 5.91; N, 13.25. Found: C, 60.96; H, 5.76; N, 12.90.

EXAMPLE 29

4-[3-Chloro-4-(1-methyl-1H-imidazol-2-ylsulfanyl)-phenylamino]-7-{[3-(dimethyl)aminopropyl]amino}-6-methoxyquinoline-3-carbonitrile Following the procedure used to prepare Example 27, 150 mg (0.34 mmol) of 4-[3-chloro-4-(1-methyl-1H-imidazol-2-ylsulfanyl)-phenylamino]-7-fluoro-6-methoxyquinoline-3-carbonitrile is reacted with 209 mg (2.05 mmol) of N,N-dimethyl-1,3-propanediamine in 1 mL of 1-methyl-2-pyrrolidinone at 105° C. for 16 hours to yield 99 mg of 4-[3-chloro-4-(1-methyl-1H-imidazol-2-ylsulfanyl)-phenylamino]-7-{[3-(dimethylamino)propyl]amino}-6-methoxyquinoline-3-carbonitrile as a tan solid, mp 198–200° C.

MS (ES, positive ion mode): m/z calcd for $C_{26}H_{28}ClN_7OS$: 521.2, found: 522.4 (M+H)⁺. Analysis for $C_{26}H_{28}ClN_7OS \cdot 0.75\ H_2O$ Calcd: C, 58.31; H, 5.55; N, 18.31 Found: C, 58.00; H, 5.16; N, 17.93.

EXAMPLE 30

4-[3-Chloro-4-(1-methyl-1H-imidazol-2-ylsulfanyl)-phenylamino]-7-{[3-(dimethylamino)propyl]-methylamino}-6-methoxyquinoline-3-carbonitrile Following the procedure used to prepare Example 27, 150 mg (0.34 mmol) of 4-[3-chloro-4-(1-methyl-1H-imidazol-2-ylsulfanyl)-phenylamino]-7-fluoro-6-methoxyquinoline-3-carbonitrile is reacted with 238 mg (2.05 mmol) of N,N'-trimethyl-1,3-propanediamine in 1 mL of 1-methyl-2-pyrrolidinone at 105° C. for 16 hours to yield 121 mg of 4-[3-chloro-4-(1-methyl-1H-imidazol-2-ylsulfanyl)-phenylamino]-7-{[3-(dimethyl)aminopropyl]-methylamino}-6-methoxyquinoline-3-carbonitrile as a tan solid, mp 196–201° C.

MS (ES, positive ion mode): m/z calcd for $C_{27}H_{30}ClN_7OS$: 535.2, found: 536.1 (M+H)⁺. Analysis for $C_{27}H_{30}ClN_7OS \cdot 0.50\ H_2O$ Calcd: C, 59.49; H, 5.73; N, 17.99. Found: C, 59.61; H, 5.59; N, 17.84.

EXAMPLE 31

4-[(2,4-Dichloro-5-methoxyphenyl)amino]-7-[3-(4-methyl)piperazin-1-yl)propoxy]-3-quinolinecarbonitrile Following the procedure used to prepare Example 15, 4-[(2,4-dichloro-5-methoxyphenyl)amino]-7-fluoro-3-quinolinecarbonitrile (200 mg, 0.55 mmol) and 3-(4-methyl)piperazin-1-yl)propanol provided 71 mg of 4-[(2,4-dichloro-5-methoxyphenyl)amino]-7-[3-(4-methyl)piperazin-1-yl)propoxy]-3-quinolinecarbonitrile, mp 154–155° C.

MS 497.9 (M-H)- Analysis for $C_{25}H_{27}Cl_2N_5O_2 \cdot 0.8\ H_2O$ Calcd: C, 58.32; H, 5.60; N, 13.60. Found: C, 58.32; H, 5.30; N, 13.28.

EXAMPLE 32

4-[(2,4-Dichloro-5-methoxyphenyl)amino]-7-[(1-methylpiperidin-4-yl)methoxy-3-quinolinecarbonitrile Following the procedure used to prepare Example 15, 4-[(2,4-dichloro-5-methoxyphenyl)amino]-7-fluoro-3-quinolinecarbonitrile (200 mg, 0.55 mmol) and 1-methyl-1-piperidine-4-methanol provides 75 mg of 4-[(2,4-dichloro-5-methoxyphenyl)amino]-7-[(1-methylpiperidin-4-yl)methoxy]-3-quinolinecarbonitrile, mp 191–193° C.

MS 468.8 (M-H)- Analysis for $C_{24}H_{24}Cl_2N_4O_2 \cdot 0.6\ H_2O$ Calcd: C, 59.78; H, 5.27; N, 11.62. Found: C, 59.87; H, 5.11; N, 11.70.

EXAMPLE 33

4-[(2,4-Dichloro-5-methoxyphenyl)amino]-7-(2-methoxyethoxy)-3-quinolinecarbonitrile Following the procedure used to prepare Example 15, 4-[(2,4-dichloro-5-methoxyphenyl)amino]-7-fluoro-3-quinolinecarbonitrile (300 mg, 0.83 mmol) and 2-(methoxy)ethanol provides 194 mg of 4-[(2,4-dichloro-5-methoxyphenyl)amino]-7-(2-methoxy)ethoxy]-3-quinolinecarbonitrile, mp 182–183° C.

MS 416.1 (M-H)- Analysis for $C_{20}H_{17}Cl_2N_3O_3$ Calcd: C, 57.43; H, 4.10; N, 10.05. Found: C, 57.36; H, 4.09; N, 9.89.

EXAMPLE 34

4-[(2,4-Dichlorophenyl)amino]-7-(2-methoxyethoxy)-3-quinolinecarbonitrile

A mixture of 4-chloro-7-(2-methoxyethoxy)-3-quinolinecarbonitrile (262 mg, 1.0 mmol), 2,4-dichloroaniline (195 mg, 1.2 mmol) and pyridine hydrochloride (140 mg, 1.2 mmol) in 10 mL of 2-ethoxyethanol is heated at reflux for 30 minutes. The reaction mixture is cooled to room temperature partitioned between ethyl acetate and saturated sodium bicarbonate. The organic layer is washed with a 1:1 mixture of saturated sodium bicarbonate and 5 N sodium hydroxide. The organic layer is dried over magnesium sulfate, filtered and concentrated in vacuo. Purification by column chromatography, eluting with a gradient of 1:1 ethyl acetate:hexane to all ethyl acetate provides 103 mg of 4-[(2,4-dichlorophenyl)amino]-7-(2-methoxyethoxy)-3-quinolinecarbonitrile, mp 144–145° C.

MS 388.0 (M−H)− Analysis for $C_{19}H_{15}Cl_2N_3O_2$ Calcd: C, 58.78; H, 3.89; N, 10.82. Found: C, 58.86; H, 3.90; N, 10.76.

EXAMPLE 35

6-Methoxy-7-(4-methylpiperazin-1-yl)-4-(4-phenoxyphenylamino)-quinoline-3-carbonitrile A reaction mixture of 0.12 g (0.38 mmol) of 4-chloro-6-methoxy-7-(4-methylpiperazin-1-yl)-quinoline-3-carbonitrile, 0.077 g (0.42 mmol) of 4-phenoxyaniline and 0.044 g (0.38 mmol) of pyridine hydrochloride in 2 ml of 2-ethoxyethanol is heated at 115° C. for 45 minutes. After cooling, the mixture is filtered, washed with cold 2-ethoxyethanol, then ethyl acetate. After drying in vacuo, the solid is suspended in a saturated solution of sodium carbonate, stirred for 45 minutes and collected by filtration. The reaction product is washed with water and dried in vacuo, to provide 0.11 g of 6-methoxy-7-(4-methylpiperazin-1-yl)-4-(4-phenoxyphenylamino)-quinoline-3-carbonitrile as a yellow solid, mp softens at 93° C.

MS(ES, negative ion mode): m/z calcd for $C_{28}H_{27}N_5O_2$: 465.2, found: 464.2 (M−H)⁻. Analysis for $C_{28}H_{27}N_5O_2 \cdot 1.0\ H_2O$ Calcd: C, 69.55; H, 6.04; N, 14.48. Found: C, 69.68; H, 5.83; N, 14.40.

The following Examples 36–40 are obtained analogously by the method of Example 17 and the corresponding alcohol.

EXAMPLE 36

4-[(2,4-Dichorophenyl)amino]-6-methoxy-7-(2-methoxyethoxy)quinoline-3-carbonitrile MP 170–171° C.; Mass spec. 415.9 (ES+)

EXAMPLE 37

4-[(2,4-Dimethyl-5-methoxyphenyl)amino]-6-methoxy-7-(2-methoxyethoxy)quinoline-3-carbonitrile MP 143–145° C.; Mass spec. 408.2 (ES+)

EXAMPLE 38

4-[(2-Chloro-5-methoxyphenyl)amino]-6-methoxy-7-(2-methoxyethoxy)quinoline-3-carbonitrile MP 179–181° C.; Mass spec. 412.2 (ES−)

EXAMPLE 39

6-Methoxy-7-(2-methoxyethoxy)-4-[(5-methoxy-2-methylphenyl)amino]-quinoline-3-carbonitrile MP 116–119° C.; Mass spec.394.2 (ES+)

EXAMPLE 40

4-[(2,4-Dimethylphenyl)amino]-6-methoxy-7-(2-methoxyethoxy)quinoline-3-carbonitrile MP 107–109° C.; Mass spec. 378.2 (ES+)

The following Examples 41–52 are obtained analogously by the method of Example 16 and the corresponding alcohol.

EXAMPLE 41

4-[(2,4-Dichlorophenyl)amino]-6-methoxy-7-[(1-methylpiperidine-4-yl)methoxy]quinoline-3-carbonitrile MP 224–225° C.; Mass spec. 469.0 (ES−)

EXAMPLE 42

4-[(2,4-Dimethyl-5-methoxyphenyl)amino]-6-methoxy-7-[(1-methylpiperidine-4-yl)methoxy]quinoline-3-carbonitrile MP 160–162° C.; Mass spec 461.3 (ES+)

EXAMPLE 43

6-Methoxy-4-[(5-methoxy-2-methylphenyl)amino]-7-[(1-methylpiperidine-4-yl)methoxy]quinoline-3-carbonitrile MP >250° C.; Mass spec. 445.2 (ES−)

EXAMPLE 44

4-[(2-Chloro-5-methoxyphenyl)amino]-6-methoxy-7-[(1-methylpiperidine-4-yl)methoxy]quinoline-3-carbonitrile MP 106–108° C.; Mass spec. 467.2 (ES+)

EXAMPLE 45

4-[(2,4-Dimethylphenyl)amino]-6-methoxy-7-[(1-methylpiperidine-4-yl)methoxy]quinoline-3-carbonitrile MP 190–191° C.; Mass spec. 429.2 (ES−)

EXAMPLE 46

4-[(2,4-Dichloro-5-methoxyphenyl)amino]-6-methoxy-7-[3-(1-methylpiperidine-4-yl)propoxy]quinoline-3-carbonitrile MP 144–145° C.; Mass spec. 529.2 (ES+)

EXAMPLE 47

4-[(2-Chloro-5-methoxyphenyl)amino]-6-methoxy-7-[3-(1-methylpiperidine-4-yl)propoxy]quinoline-3-carbonitrile MP 117–120° C.; Mass spec. 485.2 (ES+)

EXAMPLE 48

6-Methoxy-4-[(5-methoxy-2-methylphenyl)amino]-7-[3-(1-methylpiperidine-4-yl)propoxy]quinoline-3-carbonitrile MP 163–166° C.; Mass spec. 475.3 (ES+)

EXAMPLE 49

4-[(2,4-Dimethylphenyl)amino]-6-methoxy-7-[3(1-methylpiperidine-4-yl)propoxy]quinoline-3-carbonitrile MP 159–162° C.; Mass spec. 459.3 (ES+)

EXAMPLE 50

4-[(2,4-Dichloro-5-methoxyphenyl)amino]-6-methoxy-7-[3-(4-methyl-1-piperazinyl)propoxy]quinoline-3-carbonitrile MP 125–128° C.; High Resolution Mass Spec.:530.17274 calc'd: 530.17203

EXAMPLE 51

4-[(2,4-Dichloro-5-methoxyphenyl)amino]-7-[(1-ethylpiperidine-4-yl)methoxy]-6-methoxyquinoline-3-carbonitrile MP 192–195° C.; Mass spec. 515.2 (ES+)

EXAMPLE 52

4-[(2,4-Dichloro-5-methoxyphenyl)amino]-6-methoxy-7-[(1-methylpiperidine-2-yl)methoxy]quinoline-3-carbonitrile MP 178–179° C.; Mass spec. 499.0 (ES−)

Example 53 is obtained analogously by the method of Example 1 and the corresponding alcohol.

EXAMPLE 53

4-[(2,4-Dichloro-5-methoxyphenyl)amino]-6-methoxy-7-(piperidin-4-ylmethoxy)quinoline-3-carbonitrile MP 134–138° C.; Mass spec. 485.3 (ES−)

The following Examples 54–57 are obtained analogously by the method of Example 27 and the corresponding amine.

EXAMPLE 54

4-[(2,4-Dichloro-5-methoxyphenyl)amino]-7-{[3-(dimethylamino)propyl]amino}-6-methoxyquinoline-3-carbonitrile MP 165–167° C.; Mass spec. 474.1 (ES+)

EXAMPLE 55

4-[(2,4-Dichloro-5-methoxyphenyl)amino]-7-{[3-(dimethylamino)propyl](methyl)amino]-6-methoxyquinoline-3-carbonitrile MP 116–117 ° C.; Mass spec. 486.2 (ES−)

EXAMPLE 56

4-[(2,4-Dichloro-5-methoxyphenyl)amino]-6-methoxy-7-[(2-methoxyethyl)amino]quinoline-3-carbonitrile MP 165–166° C.; Mass spec. 445.1 (ES−)

EXAMPLE 57

6-Methoxy-7-(1-methyl-piperidin-4-ylmethoxy)-4-{[4-(pyridin-3-yloxy)-phenyl]amino}quinoline-3-carbonitrile Following the procedure used to prepare Reference Example 22, a mixture of 4-chloro-6- methoxy-7-[(1-methylpiperidin-4-yl)methoxy]quinoline-3-carbonitrile (200 mg, 0.58 mmol) and 4-(pyridin-3-yloxy)phenylamine (161.5 mg, 0.87 mmol) (Cacciola, J.; Fevig, J. M.; Stouten, P. F. W.; Alexander, R. S.; Knabb, R. M.; Wexler, R. W. *Bioorg. Med. Chem.* Let. 2000, 10, 1253) provides 203 mg of 6-methoxy-7-[(1-methylpiperidin-4-yl)methoxy]-4-{[4-(pyridin-3-yloxy)phenyl]amino}quinoline-3-carbonitrile, mp 182–184° C.

MS 496.3 (M+H)⁺ Analysis for $C_{29}H_{29}N_5O_3$-0.6 HCl Calcd: C, 67.30, H 5.77, N 13.54. Found: C, 67.23, H 5.65, N 13.38.

EXAMPLE 58

4-[(2,4-dichloro-5-methoxyphenyl)amino]-6-methoxy-7-{[3-(4-methylpiperazin-1-yl)propyl]amino}quinoline-3-carbonitrile

MS 529.2 (ES+)

EXAMPLE 59

4-[(2,4-dichloro-5-methoxyphenyl)amino]-6-methoxy-7-[(3-morphdin-4-ylpropyl)amino]quinoline-3-carbonitrile

MS 516.1 (ES+)

EXAMPLE 60

4-[(2,4-dichloro-5-methoxyphenyl)amino]-7-(2,2-diethoxyethoxy)-6-methoxyquinoline-3-carbonitrile

MS 506.2 (ES+)

What is claimed is:

1. A process for preparing a 7-substituted-3-quinoline or quinolone carbonitrile of Formula (I):

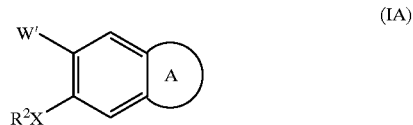

(IA)

wherein:

is a ring formula

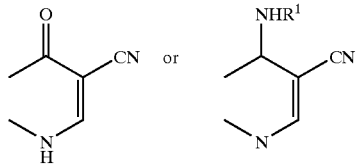

and

X is selected from —O—, —S—, —NH—, and —NR²′—;

W' is H or —OR³;

q is an integer of 0–5;

m is an integer of 0–2;

n is an integer of 2–5;

R¹ is an alkyl group of 1 to 6 carbon atoms, a cycloalkyl group of 3 to 10 carbon atoms, or an aryl, or heteroaryl ring, said aryl or heteroaryl ring is optionally fused to an additional aryl or heteroaryl ring, said aryl or heteroaryl rings optionally fused may optionally be substituted with 1 to 4 substituents independently selected from the group consisting of —J, —NO₂, —NH₂, —OH, —SH, —CN, —N₃, —COOH, —CONH₂, —NHC(O)NH₂, —C(O)H, —CF₃, —OCF₃, —R⁴, —OR⁴, —NHR⁴, —NR⁴R⁴, —S(O)ₘR⁴, —NHSO₂R⁴, —R⁵OH, —R⁵OR⁴, —R⁵NH₂, —R⁵NHR⁴, —R⁵NR⁴R⁴, —R⁵SH, —R⁵S(O)ₘR⁴, —NHR⁶OH, —N(R⁴)R⁶OH, —N(R⁴)R⁶OR⁴, —NHR⁶NH₂, —NHR⁶NHR⁴, —NHR⁶NR⁴R⁴, —N(R⁴)R⁶NH₂, —N(R⁴)R⁶NHR⁴, —N(R⁴)R⁶NHR⁴R⁴, —OR⁶OH, —OR⁶OR⁴, —OR⁶NH₂, —OR⁶NHR⁴, —OR⁶NR⁴R⁴, —OC(O)R⁴, —NHC(O)R⁴, —NHC(O)NHR⁴,

—OR⁵C(O)R⁴, —NHR⁵C(O)R⁴, —C(O)R⁴, —C(O)OR⁴, —C(O)NHR⁴, —C(O)NR⁴R⁴, —R⁵C(O)H,

—$R^5C(O)R^4$, —$R^5C(O)OH$, —$R^5C(O)OR^4$, —$R^5C(O)NH_2$, —$R^5C(O)NHR^4$, —$R^5C(O)NR^4R^4$, —$R^5OC(O)R^4$, —$R^5OC(O)NH_2$, —$R^5OC(O)NHR^4$ and —$R^5OC(O)NR^4R^4$, and —$YR^7$ groups wherein Y is independently selected from —C(O)—, —C(O)O—, —OC(O)—, —C(O)NH—, —NHC(O)—, —$NHSO_2$—, —$SO_2NH$—, —C(OH)H—, —$Q(C(R^8)_2)_q$—, —$(C(R^8)_2)_q$—, —$(C(R^8)_2)_qQ$—, —C=C—, cis- and trans —CH=CH— and cycloalkyl of 3–10 carbon atoms;

Q is —O—, —$S(O)_m$—, —NH—, or —$NR^9$—;

J is halogen selected from fluoro, chloro, bromo and iodo;

$R^2$, $R^{2'}$ and $R^3$ are each independently selected from an alkyl group of 1 to 6 carbon atoms, an alkenyl group of 2 to 6 carbon atoms or an alkynyl group of 2 to 6 carbon atoms, wherein each independent alkyl, alkenyl or alkynyl group is optionally substituted with —$NO_2$, cyano, or —$QR^4$, or $R^2$, $R^{2'}$ and $R^3$ are each independently selected from —$(C(R^8)_2)_q$-aryl, —$(C(R^8)_2)_q$-heteroaryl, —$(C(R^8)_2)_q$-heterocyclyl, —$(C(R^8)_2)_n$—Q—$(C(R^8)_2)_q$-aryl, —$(C(R^8)_2)_n$—Q—$(C(R^8)_2)_q$-heteroaryl, —$(C(R^8)_2)_n$—Q—$(C(R^8)_2)_q$-heterocyclyl, —$(C(R^8)_2)_n$—Q—$(C(R^8)_2)_n$—Q-aryl, —$(C(R^8)_2)_n$—Q—$(C(R^8)_2)_n$, —Q-heteroaryl, and —$(C(R^8)_2)_n$—Q—$(C(R^8)_2)_n$—Q-heterocyclyl, wherein the heterocyclyl group may optionally be substituted on carbon or nitrogen with a group selected from —$R^4$, —$(C(R^8)_2)_q$-aryl, —$(C(R^8)_2)_q$-heteroaryl, —$(C(R^8)_2)_q$-heterocyclyl, —$(C(R^8)_2)_q$—$SO_2R^4$, or the heterocyclyl group may optionally be substituted on carbon by —$(C(R^8)_2)_q$—$QR^4$, or the heterocyclyl group may optionally be substituted on nitrogen by —$(C(R^8)_2)_n$—$QR^4$, and also wherein the aryl or heteroaryl group may optionally be substituted with a group selected from —$NO_2$, cyano, —$R^4$, —$(C(R^8)_2)_q$-aryl, —$(C(R^8)_2)_q$-heteroaryl, —$(C(R^8)_2)_q$-heterocyclyl, —$(C(R^8)_2)_q$—$SO_2R^4$, and —$(C(R^8)_2)_q$—$QR^4$ and further provided that $R^2$ and $R^{2'}$ may optionally be taken together with the nitrogen to which they are attached, forming a heterocyclic ring having 3 to 8 ring members one of which is optionally an additional heteroatom selected from nitrogen, oxygen and sulfur, wherein said formed heterocyclic ring may optionally be substituted on carbon or nitrogen with a group —$R^4$, or said heterocyclic ring may optionally be substituted on carbon by —$(C(R^8)_2)_q$—$QR^4$, or said heterocyclic ring may optionally be substituted on nitrogen by —$(C(R^8)_2)_n$—$QR^4$;

$R^4$ is a monovalent group independently selected from alkyl of 1 to 6 carbon atoms, alkenyl of 2 to 6 carbon atoms, and alkynyl of 2 to 6 carbon atoms;

$R^5$ is a divalent group independently selected from alkyl of 1 to 6 carbon atoms, alkenyl of 2 to 6 carbon atoms, and alkynyl of 2 to 6 carbon atoms;

$R^6$ is a divalent alkyl group of 2 to 6 carbon atoms;

$R^7$ is a cycloalkyl ring of 3 to 10 carbon atoms optionally substituted with one or more alkyl groups of 1 to 6 carbon atoms or an aryl or heteroaryl ring, optionally fused to an additional aryl or heteroaryl ring, wherein said aryl or heteroaryl ring optionally fused, may optionally be substituted with 1 to 4 substituents selected from the group consisting of aryl, —$CH_2$-aryl, —NH-aryl, —O-aryl, —$S(O)_m$-aryl, —J, —$NO_2$, —$NH_2$, —OH, —SH, —CN, —$N_3$, —COOH, —$CONH_2$, —$NHC(O)NH_2$, —C(O)H, —$CF_3$, —$OCF_3$, —$R^4$, —$OR^4$, —$NHR^4$, —$NR^4R^4$, —$S(O)_mR^4$, —$NHSO_2R^4$, —$R^5OH$, —$R^5OR^4$, —$R^5NH_2$, —$R^5NHR^4$, —$R^5NR^4R^4$, —$R^5SH$, —$R^5S(O)_mR^4$, —$NHR^6OH$, —$NHR^8OR^4$, —$N(R^4)R^6OH$, —$N(R^4)R^6OR^4$, —$NHR^6NH_2$, —$NHR^6NHR^4$, —$NHR^6NR^4R^4$, —$N(R^4)R^6NH_2$, —$N(R^4)R^6NHR^4$, —$N(R^4)R^8NHR^4R^4$, —$OR^6OH$, —$OR^6OR^4$, —$OR^6NH_2$, —$OR^6NHR^4$, —$OR^6NR^4R^4$, —$OC(O)R^4$, —$NHC(O)R^4$, —$NHC(O)NHR^4$, —$OR^5C(O)R^4$, —$NHR^5C(O)R^4,C(O)R^4$, —$C(O)OR^4$, —$C(O)NHR^4$, —$C(O)NR^4R^4$, —$R^5C(O)H$, —$R^5C(O)R^4$, —$R^5C(O)OH$, —$R^5C(O)OR^4$, —$R^5C(O)NH_2$, —$R^5C(O)NHR^4$, —$R^5C(O)NR^4R^4$, —$R^5OC(O)R^4$, —$R^5OC(O)NH_2$, —$R^5OC(O)NHR^4$ and —$R^5OC(O)NR^4R^4$;

$R^8$ is independently —H or —$R^4$;

$R^9$ is a monovalent alkyl group of 1 to 6 carbon atoms;

wherein aryl as used herein denotes a mono or bi-cyclic aromatic ring having 6 to 12 carbon atoms, heteroaryl as used herein denotes a 5 or 6 membered aromatic ring, which contains 1 to 4 heteroatoms which may be the same or different selected from nitrogen, oxygen and sulfur;

and heterocyclyl denotes a saturated or partially unsaturated monocyclic radical containing 3 to 8 ring atoms selected from carbon, nitrogen, oxygen and sulfur with at least 1 and preferably 1 to 4, more preferably 1 to 2 nitrogen, oxygen or sulfur as ring atoms;

which comprises reacting a corresponding compound of Formula (IIA)

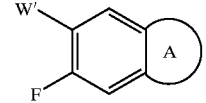

(IIA)

wherein:

is as defined above; with a compound of the formula $R^2XH$, where X is selected from —S—, —O—, —NH—, and —$NR^{2'}$— and where $R^{2'}$ and $R^2$ are as defined above or $R^{2'}$ and $R^2$ may optionally be taken together with the nitrogen to which each is attached to form a heterocyclic ring, and in the presence of a base, when X is —O— or —S—, to provide a 7-substituted-3-quinolinecarbonitrile of Formula (IA)

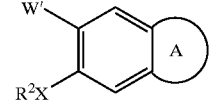

(IA)

and if so desired converting a compound of Formula (IA) to a corresponding pharmaceutically acceptable salt by conventional means, and if so desired, converting the corresponding pharmaceutically acceptable salt to a compound of Formula (IA) by conventional means.

2. A process according to claim 1 in which the compound of formula IIA used as starting material is a 7-fluoro-4-(substituted amino)-3-quinolinecarbonitrile of formula 2

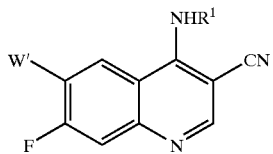

which is prepared by a process comprising the following steps:
 a) reacting a 7-fluoro-4-oxo-1,4-dihydro-3-quinolinecarbonitrile of Formula (II)

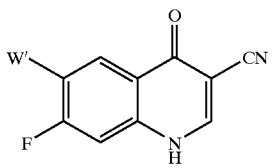

with a halogenating reagent to provide a 7-fluoro-3-quinolinecarbonitrile 1 where Z is Cl or Br

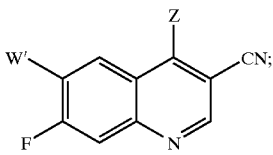

and
 b) reacting the 7-fluoro-3-quinolinecarbonitrile product of formula 1 with an amine of the formula $R^1NH_2$ in the presence of pyridine hydrochloride to provide a 7-fluoro-4-(substituted amino)-3-quinolinecarbonitrile of formula 2

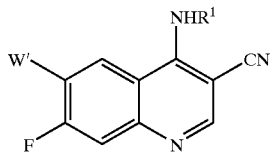

as defined in claim 1.

3. A process according to claim 1 in which the product of formula (IA) is a 7-substituted-4-oxo-1,4-dihydro-3-quinolinecarbonitrile of Formula 3

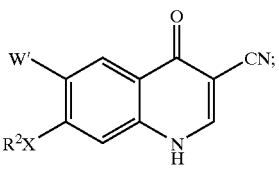

and this is converted to a compound of formula (I) by process comprising the following steps:

a) reacting with a halogenating reagent to provide a 7-substituted-4-halo-3-quinolinecarbonitrile 4 where Z is Cl or Br

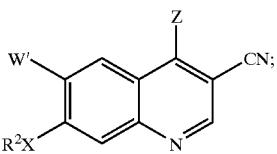

b) reacting the 7-substituted-4-halo-3-quinolinecarbonitrile of step a) with an amine $R^1NH_2$ in the presence of pyridine hydrochloride to afford a 7-substituted-3-quinolinecarbonitrile of Formula (I)

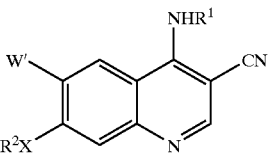

and if so desired converting a compound of Formula (I) to a corresponding pharmaceutically acceptable salt by conventional means, and if so desired, converting the corresponding pharmaceutically acceptable salt to a compound of Formula (I) by conventional means.

4. A process according to any one of claims 1 to 3 wherein the halogenating reagent is phosphorous oxychloride or phosphorous oxybromide.

5. A process according to any one of claims 1 to 4 wherein $R^1$ is substituted aryl.

6. A process according to any one of claims 1 to 4 wherein $R^1$ is selected from
 2,4-dichloro-5-methoxyphenyl;
 Cyclopentyl;
 Butyl;
 3,4,5-trimethoxyphenyl;
 3-Chloro-4-(1-methyl-1H-imidazol-2-yl)sulfanyl]phenyl;
 2,4-Dichorophenyl;
 2-Chloro-5-methoxyphenyl;
 5-methoxy-2-methylphenyl and
 2,4-Dimethylphenyl.

7. A process according to any one of claims 1 to 6 wherein X is —O— or —S— and wherein said base is selected from potassium, potassium hydride, sodium and sodium hydride.

8. A process according to claim 7 wherein said base is sodium or sodium hydride.

9. A process according to any one of claims 1 to 8 wherein $R^2$ is selected from one of the following:
 2-butynyl;
 3-dimethylamino-2,2-dimethylpropyl;
 3-(1,1-dioxido-4-thiomorpholinyl)propyl;
 2-[2-(1-piperazinyl)ethoxy]ethyl;
 2-thienylmethyl;
 benzyl; ethyl;
 phenyl;
 2-methoxyethyl;
 pyridin-4-yl;
 2-(1-methylpiperidin-4-yl)ethyl;
 2-(1-methyl-3-piperidinyl)methyl 2-(1-methyl-4-piperidinyl)methyl;
2-(2-methoxy)ethyl;
3-(dimethylamino)propyl;
3-(4-ethyl-1-piperazinyl)propyl;
(1-methylpiperidine-4-yl)methyl;
tetrahydro-2H-pyran-2-ylmethyl;
3-(1-methylpiperidin-4-yl)propyl;
(3-(dimethylamino)propyl)methyl
(1-methylpiperidin-4-yl)methyl;
3-(1-methylpiperidine-4-yl)propyl;
3-(4-methyl-1-piperazinyl)propyl;
(1-ethylpiperidine-4-yl)methyl;
(1-methylpiperidine-2-yl)methyl;
piperidin-4-ylmethyl; and
3-(dimethylamino)propyl.

10. A process according to to any one of claims 1 to 6 wherein X is —NH— or —NR$^{2'}$— and where R$^{2'}$ and R$^2$ may optionally be taken together with the nitrogen to which each is attached to form a heterocyclic ring.

11. A process according to claim 10 wherein XR$^2$ is selected from 4-methylpiperazin-1-yl or (4-pyrrolidin-1-ylpiperidin-1-yl).

12. A process according to any one of claims 1 to 4 for the preparation of a compound selected from the group consisting of:

7-(2-Butynyloxy)-4-[(2,4-dichloro-5-methoxyphenyl)amino]-6-methoxy-3-quinolinecarbonitrile;
4-[(2,4-Dichloro-5-methoxyphenyl)amino]-7-(3-dimethylamino-2,2-dimethylpropoxy)-6-methoxy-3-quinolinecarbonitrile;
4-[(2,4-Dichloro-5-methoxyphenyl)amino]-7-[3-(1,1-dioxido-4-thiomorpholinyl)propoxy]-6-methoxy-3-quinolinecarbonitrile;
4-[(2,4-Dichloro-5-methoxyphenyl)amino]-6-methoxy-7-{2-[2-(1-piperazinyl)ethoxy]ethoxy}-3-quinolinecarbonitrile;
4-[(2,4-Dichloro-5-methoxyphenyl)amino]-6-methoxy-7-(2-thienylmethoxy)-3-quinolinecarbonitrile;
7-Benzyloxy-4-[(2,4-dichloro-5-methoxyphenyl)amino]-6-methoxy-3-quinolinecarbonitrile;
4-[(2,4-Dichloro-5-methoxyphenyl)amino]-7-ethylsulfanyl-6-methoxy-3-quinolinecarbonitrile;
4-[(2,4-Dichloro-5-methoxyphenyl)amino]-6-methoxy-7-phenylsulfanyl-3-quinolinecarbonitrile;
4-Cyclopentylamino-6-methoxy-7-(2-methoxyethoxy)-3-quinolinecarbonitrile;
4-Butylamino-6-methoxy-7-(2-methoxyethoxy)-3-quinolinecarbonitrile;
7-Benzylthio-4-[(2,4-dichloro-5-methoxyphenyl)amino]-6-methoxy-3-quinolinecarbonitrile;
4-[(2,4-Dichloro-5-methoxyphenyl)amino]-6-methoxy-7-(pyridin-4-yloxy)-3-quinolinecarbonitrile;
4-[(2,4-Dichloro-5-methoxyphenyl)amino]-6-methoxy-7-[2-(1-methylpiperidin-4-yl)ethoxy]-3-quinolinecarbonitrile;
4-[(2,4-Dichloro-5-methoxyphenyl)amino]-6-methoxy-7-[2-methoxyethoxy]-3-quinolinecarbonitrile;
4-[(2,4-Dichloro-5-methoxyphenyl)amino]-6-methoxy-7-[2-(1-methyl-3-piperidinyl)methoxy]-3-quinolinecarbonitrile;
4-[(2,4-Dichloro-5-methoxyphenyl)amino]-6-methoxy-7-[2-(1-methyl-4-piperidinyl)methoxy]-3-quinolinecarbonitrile;
6-Methoxy-7-[2-methoxyethoxy]-4-[(3,4,5-trimethoxyphenyl)amino]-3-quinolinecarbonitrile;
6-Methoxy-7-[(1-methylpiperidine-4-yl)methoxy]-4-[(3,4,5-trimethoxyphenyl)amino]-3-quinolinecarbonitrile;
4-({3-Chloro-4-[(1-methyl-1H-imidazol-2-yl)sulfanyl]phenyl}amino)-6-methoxy-7-[2-(2-methoxy)ethoxy]-3-quinolinecarbonitrile;
4-({3-Chloro-4-[(1-methyl-1H-imidazol-2-yl)sulfanyl]phenyl}amino)-7-[3-(dimethylamino)propoxy]-6-(2-methoxyethoxy)-3-quinolinecarbonitrile;
4-({3-Chloro-4-[(1-methyl-1H-imidazol-2-yl)sulfanyl]phenyl}amino)-7-[3-(4-ethyl-1-piperazinyl)propoxy]-6-(2-methoxyethoxy)-3-quinolinecarbonitrile;
4-[(2,4-Dichloro-5-methoxyphenyl)amino]-6-[2-methoxyethoxy]-7-[(1-methylpiperidine-4-yl)methoxy]3-quinolinecarbonitrile;
4-[(2,4-Dichloro-5-methoxyphenyl)amino]-6-ethoxy-7-(2-methoxyethoxy)3-quinolinecarbonitrile;
4-[(2,4-Dichloro-5-methoxyphenyl)amino]-6-methoxy-7-(tetrahydro-2H-pyran-2-ylmethoxy)3-quinolinecarbonitrile;
4-[(2,4-Dichloro-5-methoxyphenyl)amino]-7-(2-methoxyethoxy)-6-(2-morpholin-4-ylethoxy)3-quinolinecarbonitrile;
4-[3-Chloro-4-(1-methyl-1H-imidazol-2-ylsulfanyl)-phenylamino]-6-methoxy-7-(4-methylpiperazin-1-yl)-quinoline-3-carbonitrile;
4-[(2,4-Dichloro-5-methoxyphenyl)amino]-6-methoxy-7-{[3-(1-methylpiperidin-4-yl)propyl]amino}quinoline-3-carbonitrile;
4-[3-Chloro-4-(1-methyl-1H-imidazol-2-ylsulfanyl)-phenylamino]-7-{[3-(dimethyl)aminopropyl]amino}-6-methoxyquinoline-3-carbonitrile;
4-[3-Chloro-4-(1-methyl-1H-imidazol-2-ylsulfanyl)-phenylamino]-7-{[3-(dimethylamino)propyl]-methylamino}-6-methoxyquinoline-3-carbonitrile;
4-[(2,4-Dichloro-5-methoxyphenyl)amino]-7-[3-(4-methyl)piperazin-1-yl)propoxy]-3-quinolinecarbonitrile;
4-[(2,4-Dichloro-5-methoxyphenyl)amino]-7-[(1-methylpiperidin-4-yl)methoxy]-3-quinolinecarbonitrile;
4-[(2,4-Dichloro-5-methoxyphenyl)amino]-7-(2-methoxyethoxy)-3-quinolinecarbonitrile;
4-[(2,4-Dichorophenyl)amino]-6-methoxy-7-(2-methoxyethoxy)quinoline-3-carbonitrile;
4-[(2,4-Dimethyl-5-methoxyphenyl)amino]-6-methoxy-7-(2-methoxyethoxy)quinoline-3-carbonitrile;
4-[(2-Chloro-5-methoxyphenyl)amino]-6-methoxy-7-(2-methoxyethoxy)quinoline-3-carbonitrile;
6-Methoxy-7-(2-methoxyethoxy)-4-[(5-methoxy-2-methylphenyl)amino]-quinoline-3-carbonitrile;
4-[(2,4-Dimethylphenyl)amino]-6-methoxy-7-(2-methoxyethoxy)quinoline-3-carbonitrile;
4-[(2,4-Dichlorophenyl)amino]-6-methoxy-7-[(1-methylpiperidine-4-yl)methoxy]quinoline-3-carbonitrile;
4-[(2,4-Dimethyl-5-methoxyphenyl)amino]-6-methoxy-7-[(1-methylpiperidine-4-yl)methoxy]quinoline-3-carbonitrile;
6-Methoxy-4-[(5-methoxy-2-methylphenyl)amino]-7-[(1-methylpiperidine-4-yl)methoxy]quinoline-3-carbonitrile;

4-[(2-Chloro-5-methoxyphenyl)amino]-6-methoxy-7-[(1-methylpiperidine-4-yl)methoxy]quinoline-3-carbonitrile;

4-[(2,4-Dimethylphenyl)amino]-6-methoxy-7-[(1-methylpiperidine-4-yl)methoxy]quinoline-3-carbonitrile;

4-[(2,4-Dichloro-5-methoxyphenyl)amino]-6-methoxy-7-[3-(1-methylpiperidine-4-yl)propoxy]quinoline-3-carbonitrile;

4-[(2-Chloro-5-methoxyphenyl)amino]-6-methoxy-7-[3-(1-methylpiperidine-4-yl)propoxy]quinoline-3-carbonitrile;

6-Methoxy-4-[(5-methoxy-2-methylphenyl)amino]-7-[3-(1-methylpiperidine-4-yl)propoxy]quinoline-3-carbonitrile;

4-[(2,4-Dimethylphenyl)amino]-6-methoxy-7-[3(1-methylpiperidine-4-yl)propoxy]quinoline-3-carbonitrile;

4-[(2,4-Dichloro-5-methoxyphenyl)amino]-6-methoxy-7-[3-(4-methyl-1-piperazinyl)propoxy]quinoline-3-carbonitrile;

4-[(2,4-Dichloro-5-methoxyphenyl)amino]-7-[(1-ethylpiperidine-4-yl)methoxy]-6-methoxyquinoline-3-carbonitrile;

4-[(2,4-Dichloro-5-methoxyphenyl)amino]-6-methoxy-7-[(1-methylpiperidine-2-yl)methoxy]quinoline-3-carbonitrile;

4-[(2,4-Dichloro-5-methoxyphenyl)amino]-6-methoxy-7-(piperidin-4-ylmethoxy)quinoline-3-carbonitrile;

4-[(2,4-Dichloro-5-methoxyphenyl)amino]-7-{[3-(dimethylamino)propyl]amino}-6-methoxyquinoline-3-carbonitrile;

4-[(2,4-Dichloro-5-methoxyphenyl)amino]-7-{[3-(dimethylamino)propyl](methyl)amino]-6-methoxyquinoline-3-carbonitrile; and 4-[(2,4-Dichloro-5-methoxyphenyl)amino]-6-methoxy-7-[(2-methoxyethyl)amino]quinoline-3-carbonitrile.

13. A process according to claim 1 for the preparation of a compound selected from the group consisting of:

4-[(2,4-Dichlorophenyl)amino]-7-(2-methoxyethoxy)quinoline-3-carbonitrile;

6-Butoxy-4-[(2,4-dichloro-5-methoxyphenyl)amino]-7-(2-methoxyethoxy)-3-quinolinecarbonitrile;

6-Methoxy-7-(4-methylpiperazin-1-yl)-4-(4-phenoxyphenylamino)-quinoline-3-carbonitrile;

4-[(2,4-dichloro-5-methoxyphenyl)amino]-6-methoxy-7-{[3-(4-methylpiperazin-1-yl)propyl]amino}quinoline-3-carbonitrile;

4-[(2,4-dichloro-5-methoxyphenyl)amino]-6-methoxy-7-[(3-morphdin-4-ylpropyl)amino]quinoline-3-carbonitrile;

4-[(2,4-dichloro-5-methoxyphenyl)amino]-7-(2,2-diethoxyethoxy)-6-methoxyquinoline-3-carbonitrile; and 6-Methoxy-7-(1-methyl-piperidin-4-ylmethoxy)-4-{[4-(pyridin-3-yloxy)-phenyl]amino}quinoline-3-carbonitrile.

14. A process according to claim 1 for the preparation of a compound selected from the group consisting of:

6-Methoxy-7-(2-methoxyethoxy)-4-oxo-1,4,-dihydro-3-quinolinecarbonitrile;

6-Methoxy-7-(4-methyl-piperazin-1-yl)-4-oxo-1,4-dihydroquinoline-3-carbonitrile; and 7-(2-Methoxyethoxy)-4-oxo-1,4-dihydroquinoline-3-carbonitrile.

* * * * *

UNITED STATES PATENT AND TRADEMARK OFFICE
CERTIFICATE OF CORRECTION

PATENT NO. : 6,780,996 B2
DATED : August 24, 2004
INVENTOR(S) : Diane H. Boschelli et al.

It is certified that error appears in the above-identified patent and that said Letters Patent is hereby corrected as shown below:

Column 44,
Line 5, replace "$-NHR^8OR^4$" with -- $-NHR^6OR^4$ --
Line 8, replace "$-N(R^4)R^8NHR^4R^4$" with -- $-N(R^4)R^6NHR^4R^4$ --

Signed and Sealed this

First Day of March, 2005

JON W. DUDAS
*Director of the United States Patent and Trademark Office*